United States Patent [19]
Gorman et al.

[11] Patent Number: 6,111,090
[45] Date of Patent: Aug. 29, 2000

[54] MAMMALIAN CELL SURFACE ANTIGENS; RELATED REAGENTS

[75] Inventors: Daniel M. Gorman, Newark, Calif.; Troy D. Randall, Saranac Lake, N.Y.; Albert Zlotnik, Palo Alto, Calif.

[73] Assignee: Schering Corporation, Kenilworth, N.J.

[21] Appl. No.: 08/911,423

[22] Filed: Aug. 14, 1997

Related U.S. Application Data

[60] Provisional application No. 60/023,419, Aug. 16, 1996, and provisional application No. 60/027,901, Oct. 7, 1996.

[51] Int. Cl.[7] .............................. C07H 21/04; C12N 5/10; C12N 15/12; C12N 15/63
[52] U.S. Cl. ....................... 536/23.5; 435/69.1; 435/91.1; 435/252.3; 435/320.1; 435/455; 435/810; 514/44; 530/350; 530/326
[58] Field of Search .................................. 435/69.1, 91.1, 435/252.3, 320.1, 455, 810; 514/44; 530/350, 326; 536/23.5

[56] References Cited

U.S. PATENT DOCUMENTS 5,457,035  10/1995  Baum et al. .

FOREIGN PATENT DOCUMENTS

WO 91/06644  5/1991  WIPO .
WO 96/15272  5/1996  WIPO .

OTHER PUBLICATIONS

Richard J. Armitage, et al., *Nature*, 357: 80–82, 1992. "Molecular and biological characterization of a murine ligand for CD40".

Charles Auffray, et al., C.R. Acad. Sci. Paris, 318(2):263–272, 1995. Abstract only "IMAGE: molecular integration of the analysis of the human genome and its expression".

C. Auffray, et al., *GenBank*, Accession No. F09449, Sep. 21, 1995. "IMAGE: molecular integration of the analysis of the human genome and its expression".

Peter R. Baum, et al., Circulatory Shock, 44(1):30–34, 1994. "Identification of OX40 Ligand and Preliminary Characterization of Its Activities on OX40 Receptor".

P.R. Baum, et al., *GenBank*, Entrez Protein Query, GenPept Report, Accession No. 1252423, Oct. 12, 1995. "Cytokine which is a ligand for OX40".

P.R. Baum, et al., *GenBank*, Accession No. S76792, Jul. 26, 1995. "Identification of OX40 ligand and preliminary characterization of its activities on OX40 receptor".

G.I. Bell, *GenBank*, Accession No. Z11899, Jun. 4, 1996. DEFINITION: H. sapiens OTF3 mRNA encoding octomer––binding protein 3B.

G.I. Bell, *GenBank*, Accession No. Z11901, Jun. 25, 1997. DEFINITION: H. sapiens OTF3 gene encoding octomer binding protein 3–like sequence.

Barbara E. Bierer, et al., *Semin. Immunol.*, 5:249–261, (1993). "T cell adhesion, avidity regulation and signaling: a molecular analysis of CD2".

Marion L. Birkeland, et al., *Eur. J. Immunol.*, 25(4):926–930, 1995. "Gene structure and chromosomal localization of the mouse homologue of rat OX40 protein".

M.L. Birkeland, et al., *GenBank*, Accession No. X85214, Aug. 23, 1995. "Gene structure and chromosomal localization of the mouse homologue of rat OX40 protein".

David M. Calderhead, et al., *J. Immunol.*, 151(10)5261–5271, 1993. "Cloning of mouse Ox40: a T cell activation marker that may mediate T–B cell interactions".

D.M. Calderhead, et al., *GenBank*, Accession No. Z21674, Dec. 20, 1993. "Cloning of mouse Ox40: a T cell activation marker that may mediate T–B cell interactions".

Benjamin G. Cocks, et al., *Int. Immunol.*, 5(6):657–663, (1993). "IL–13 induces proliferation and differentiation of human B cells activated by the CD40 ligand".

Benjamin G. Cocks, et al., *Nature*, 376: 260–263, (1995). "A novel receptor involved in T–cell activation".

Jonathan M. Green, et al., *Immunity*, 1:501–508, (1994). "Absence of B7–Dependent Responses in CD28–Deficient Mice".

Marc K. Jenkins, et al., *Curr. Opin. Immunol.*, 5:361–367, (1993). "Molecules involved in T–cell costimulation".

Marc K. Jenkins, *Immunity*, 1:443–446, (1994). "The Ups and Downs of T Cell Costimulation".

Carl H. June, et al., *Immunol. Today*, 11(6):211–216, (1990). "Role of the CD28 receptor in T–cell activation".

Matthew F. Krummel, et al., *J. Exp. Med.*, 182: 459–465, (1995). "CD28 and CTLA–4 Have Opposing Effects on the Response of T cells to Stimulation".

Ute Latza, et al., *Eur. J. Immunol.*, 24(3):677–683, 1994. "The human OX40 homolog: cDNA structure, expression and chromosomal assignment of the ACT35 antigen".

U. Latza, et al., *GenBank*, Accession No. X75962, May 13, 1994. "The human OX40 homolog: cDNA structure, expression and chromosomal assignment of the ACT35 antigen".

M. Marra, et al., *GenBank*, Accession No. AA023897, Jan. 21, 1997. "The WashU–HHMI Mouse EST Project".

M. Marra, et al., *GenBank*, Accession No. W98639, Jul. 16, 1996. "The WashU–HHMI Mouse EST Project".

Franca Ronchese, et al., *J. Exp. Med.*, 179: 809–817, (1994). "Mice Transgenic for a Soluble Form of Murine CTLA–4 Show Enhanced Expansion of Antigen–specific CD4+ T Cells and Defective Antibody Production In Vivo".

(List continued on next page.)

*Primary Examiner*—David Saunders
*Assistant Examiner*—Mary Beth Tung
*Attorney, Agent, or Firm*—Gerald P. Keleher; Sheela Mohan-Peterson; Edwin P. Ching

[57] ABSTRACT

Purified genes encoding a T cell surface antigen from a mammal, reagents related thereto including purified proteins, specific antibodies, and nucleic acids encoding this antigen are provided. Methods of using said reagents and diagnostic kits are also provided.

36 Claims, No Drawings

OTHER PUBLICATIONS

Eric Rouvier, et al., *J. Immunol.*, 150(12): 5445–5456, (1993). "CTLA–8, Cloned from an Activated T Cell, Bearing AU–Rich Messenger RNA Instability Sequences, and Homologous to a Herpes virus Saimiri Gene[1]".

Meenakshi Roy, et al., *Eur. J. Immunol.*, 25: 596–603, (1995). "Studies on the interdependence of gp39 and B7 expression and function during antigen–specific immune responses".

Joseph Sambrook, et al., *Molecular Cloning, A Laboratory Manual*, 2nd Ed., Cold Spring Harbor Laboratory Press, 1989, pp. 11.2, and 17.2–17.29.

Arda Shahinian, et al., *Science*, 261: 609–612, (1993). "Differential T Cell Costimulatory Requirements in CD28–Deficient Mice".

Jun Takeda, et al., *Nucleic Acids Research*, 20(17):4613–4620, 1992. "Human Oct3 gene family: cDNA sequences, alternative splicing, gene organization, chromosomal location, and expression at low levels in adult tissues".

J. Takeda, et al., *GenBank*, Accession No. Z11898, Sep. 28, 1992. "Human Oct3 gene family: cDNA sequences, alternative splicing, gene organization, chromosomal location, and expression at low levels in adult tissues".

J. Takeda, et al., *GenBank*, Accession No. Z11900, Jun. 25, 1997. "Human Oct3 gene family: cDNA sequences, alternative splicing, gene organization, chromosomal location, and expression in adult tissues".

Eva Wey, et al., *Eur. J. Biochem.*, 220(3):753–762, 1994. "A human POU domain gene, mPOU, is expressed in developing brain and specific adult tissues".

E. Wey, et al., *GenBank*, Accession No. Z21963, Jun. 27, 1994. "A human POU domain gene, mPOU, is expressed in developing brain and specific adult tissues".

E. Wey, et al., *GenBank*, Accession No. Z21963, Jun. 27, 1994. "mPOU: A novel human POU domain gene expressed in specific adult tissues".

Matoba, R, et al., The addition of 5'–coding informatio to a 3'–directed cDNA library improves analysis of gene expression. Gene, 146:199–207, Dec. 1994.

Matoba, r, et al., GenBank Accession No. D17247, Dec. 1, 1994.

Gregory S. Kelner, et al., *Science*, 266:1395–1399, Nov. 25, 1994. "Lymphotactin: A New Cytokine That Represents a New Class of Chemokine".

T. Newman, et al., *EMBL Sequence Database*, Accession No. T22298, Jun. 27, 1994. "Genes galore: a summary of methods for accessing results from large–scale partial sequencing of anonymous Arabidopsis cDNA clones".

Christine A. Power and Timothy N.C. Wells, *TIPS*, 17(6):209–213, Jun. 1996. "Cloning and characterization of human chemokine receptors".

A. Ruehlmann, et al., *EMBL Sequence Database*, Accession No. X75316, Oct. 12, 1993. "A novel murine RRM–type protein and its human homologue".

E.A. Telford, et al., *EMBL Sequence Database*, Accession No. U20824, May 4, 1995. "The DNA sequence of equine herpes virus 2".

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 1073 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 68..751

(xi) SEQUENCE DESCRIPTION: SEQ ID NO:1:

```
CTCGAGATCC ATTGTGCTGG AAAGGGAACT CCTGAAATCA GCCGACAGAA GACTCAGGAG        60

AAGCACT ATG GGG GCA TGG GCC ATG CTG TAT GGA GTC TCG ATG CTC TGT        109
        Met Gly Ala Trp Ala Met Leu Tyr Gly Val Ser Met Leu Cys
          1               5                  10

GTG CTG GAC CTA GGT CAG CCG AGT GTA GTT GAG GAG CCT GGC TGT GGC        157
Val Leu Asp Leu Gly Gln Pro Ser Val Val Glu Glu Pro Gly Cys Gly
 15                  20                  25                  30

CCT GGC AAG GTT CAG AAC GGA AGT GGC AAC AAC ACT CGC TGC TGC AGC        205
Pro Gly Lys Val Gln Asn Gly Ser Gly Asn Asn Thr Arg Cys Cys Ser
                 35                  40                  45

CTG TAT GCT CCA GGC AAG GAG GAC TGT CCA AAA GAA AGG TGC ATA TGT        253
Leu Tyr Ala Pro Gly Lys Glu Asp Cys Pro Lys Glu Arg Cys Ile Cys
             50                  55                  60

GTC ACA CCT GAG TAC CAC TGT GGA GAC CCT CAG TGC AAG ATC TGC AAG        301
Val Thr Pro Glu Tyr His Cys Gly Asp Pro Gln Cys Lys Ile Cys Lys
         65                  70                  75

CAC TAC CCC TGC CAA CCA GGC CAG AGG GTG GAG TCT CAA GGG GAT ATT        349
His Tyr Pro Cys Gln Pro Gly Gln Arg Val Glu Ser Gln Gly Asp Ile
     80                  85                  90

GTG TTT GGC TTC CGG TGT GTT GCC TGT GCC ATG GGC ACC TTC TCC GCA        397
Val Phe Gly Phe Arg Cys Val Ala Cys Ala Met Gly Thr Phe Ser Ala
 95                 100                 105                 110

GGT CGT GAC GGT CAC TGC AGA CTT TGG ACC AAC TGT TCT CAG TTT GGA        445
Gly Arg Asp Gly His Cys Arg Leu Trp Thr Asn Cys Ser Gln Phe Gly
                115                 120                 125

TTT CTC ACC ATG TTC CCT GGG AAC AAG ACC CAC AAT GCT GTG TGC ATC        493
Phe Leu Thr Met Phe Pro Gly Asn Lys Thr His Asn Ala Val Cys Ile
            130                 135                 140

CCG GAG CCA CTG CCC ACT GAG CAA TAC GGC CAT TTG ACT GTC ATC TTC        541
Pro Glu Pro Leu Pro Thr Glu Gln Tyr Gly His Leu Thr Val Ile Phe
        145                 150                 155

CTG GTC ATG GCT GCA TGC ATT TTC TTC CTA ACC ACA GTC CAG CTC GGC        589
```

```
Leu Val Met Ala Ala Cys Ile Phe Phe Leu Thr Thr Val Gln Leu Gly
            160                 165                 170

CTG CAC ATA TGG CAG CTG AGG AGG CAA CAC ATG TGT CCC CGA GAG ACC        637
Leu His Ile Trp Gln Leu Arg Arg Gln His Met Cys Pro Arg Glu Thr
175                 180                 185                 190

CAG CCA TTC GCG GAG GTG CAG TTG TCA GCT GAG GAT GCT TGC AGC TTC        685
Gln Pro Phe Ala Glu Val Gln Leu Ser Ala Glu Asp Ala Cys Ser Phe
                195                 200                 205

CAG TTC CCT GAG GAG GAA CGC GGG GAG CAG ACA GAA GAA AAG TGT CAT        733
Gln Phe Pro Glu Glu Glu Arg Gly Glu Gln Thr Glu Glu Lys Cys His
            210                 215                 220

CTG GGG GGT CGG TGG CCA TGAGGCCTGG TCTTCCTCTG TGCCCCAAGC               781
Leu Gly Gly Arg Trp Pro
            225

CAGACGCTAC AAGACTTGCC CAGCTATACC CTTGGTGAGA GCAGGGGCCA TGCTCTGCAC       841

CCTTCCCTGG GCCTGGCCCT GCTCCCCTCA ACAGTGGCGG AAGTGGGTGT ATGAGAGCGG       901

TGAGTTACGA TTGGGCCCTA TGGCTGCCTT TCTCATTTGA CAGCTCTGTT GGAGTAGGGT       961

CTTTGGGCCC ACCAAGAGCA CCACGTTTAG CACAAGATCT TGTACAAGAA TAAATACTTG      1021

TTTAGTAACC TGAAAAAAAA AAAAAAAGG GCGGCCGCGG AGGCCGAATT CC              1073

(2) INFORMATION FOR SEQ ID NO:2:

(i) SEQUENCE CHARACTERISTICS:
        (A) LENGTH: 228 amino acids
        (B) TYPE: amino acid
        (D) TOPOLOGY: linear (ii) MOLECULE TYPE: protein (xi) SEQUENCE DESCRIPTION: SEQ ID NO:2:

Met Gly Ala Trp Ala Met Leu Tyr Gly Val Ser Met Leu Cys Val Leu
1               5                   10                  15

Asp Leu Gly Gln Pro Ser Val Val Glu Glu Pro Gly Cys Gly Pro Gly
            20                  25                  30

Lys Val Gln Asn Gly Ser Gly Asn Asn Thr Arg Cys Cys Ser Leu Tyr
        35                  40                  45

Ala Pro Gly Lys Glu Asp Cys Pro Lys Glu Arg Cys Ile Cys Val Thr
    50                  55                  60

Pro Glu Tyr His Cys Gly Asp Pro Gln Cys Lys Ile Cys Lys His Tyr
65                  70                  75                  80

Pro Cys Gln Pro Gly Gln Arg Val Glu Ser Gln Gly Asp Ile Val Phe
                85                  90                  95

Gly Phe Arg Cys Val Ala Cys Ala Met Gly Thr Phe Ser Ala Gly Arg
            100                 105                 110

Asp Gly His Cys Arg Leu Trp Thr Asn Cys Ser Gln Phe Gly Phe Leu
        115                 120                 125

Thr Met Phe Pro Gly Asn Lys Thr His Asn Ala Val Cys Ile Pro Glu
    130                 135                 140

Pro Leu Pro Thr Glu Gln Tyr Gly His Leu Thr Val Ile Phe Leu Val
145                 150                 155                 160

Met Ala Ala Cys Ile Phe Phe Leu Thr Thr Val Gln Leu Gly Leu His
                165                 170                 175

Ile Trp Gln Leu Arg Arg Gln His Met Cys Pro Arg Glu Thr Gln Pro
            180                 185                 190

Phe Ala Glu Val Gln Leu Ser Ala Glu Asp Ala Cys Ser Phe Gln Phe
        195                 200                 205
```

```
Pro Glu Glu Glu Arg Gly Glu Gln Thr Glu Glu Lys Cys His Leu Gly
    210                 215                 220

Gly Arg Trp Pro
225

(2) INFORMATION FOR SEQ ID NO:3:

(i) SEQUENCE CHARACTERISTICS:
         (A) LENGTH: 1006 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: CDS
         (B) LOCATION: 1..723

(xi) SEQUENCE DESCRIPTION: SEQ ID NO:3:

ATG GCA CAG CAC GGG GCG ATG GGC GCG TTT CGG GCC CTG TGC GGC CTG      48
Met Ala Gln His Gly Ala Met Gly Ala Phe Arg Ala Leu Cys Gly Leu
  1               5                  10                  15

GCG CTG CTG TGC GCG CTC AGC CTG GGT CAG CGC CCC ACC GGG GGT CCC      96
Ala Leu Leu Cys Ala Leu Ser Leu Gly Gln Arg Pro Thr Gly Gly Pro
             20                  25                  30

GGG TGC GGC CCT GGG CGC CTC CTG CTT GGG ACG GGA ACG GAC GCG CGC     144
Gly Cys Gly Pro Gly Arg Leu Leu Leu Gly Thr Gly Thr Asp Ala Arg
         35                  40                  45

TGC TGC CGG GTT CAC ACG ACG CGC TGC TGC CGC GAT TAC CCG GGC GAG     192
Cys Cys Arg Val His Thr Thr Arg Cys Cys Arg Asp Tyr Pro Gly Glu
     50                  55                  60

GAG TGC TGT TCC GAG TGG GAC TGC ATG TGT GTC CAG CCT GAA TTC CAC     240
Glu Cys Cys Ser Glu Trp Asp Cys Met Cys Val Gln Pro Glu Phe His
 65                  70                  75                  80

TGC GGA GAC CCT TGC TGC ACG ACC TGC CGG CAC CAC CCT TGT CCC CCA     288
Cys Gly Asp Pro Cys Cys Thr Thr Cys Arg His His Pro Cys Pro Pro
                 85                  90                  95

GGC CAG GGG GTA CAG TCC CAG GGG AAA TTC AGT TTT GGC TTC CAG TGT     336
Gly Gln Gly Val Gln Ser Gln Gly Lys Phe Ser Phe Gly Phe Gln Cys
            100                 105                 110

ATC GAC TGT GCC TCG GGG ACC TTC TCC GGG GGC CAC GAA GGC CAC TGC     384
Ile Asp Cys Ala Ser Gly Thr Phe Ser Gly Gly His Glu Gly His Cys
        115                 120                 125

AAA CCT TGG ACA GAC TGC ACC CAG TTC GGG TTT CTC ACT GTG TTC CCT     432
Lys Pro Trp Thr Asp Cys Thr Gln Phe Gly Phe Leu Thr Val Phe Pro
    130                 135                 140

GGG AAC AAG ACC CAC AAC GCT GTG TGC GTC CCA GGG TCC CCG CCG GCA     480
Gly Asn Lys Thr His Asn Ala Val Cys Val Pro Gly Ser Pro Pro Ala
145                 150                 155                 160

GAG CCG CTT GGG TGG CTG ACC GTC GTC CTC CTG GCC GTG GCC GCC TGC     528
Glu Pro Leu Gly Trp Leu Thr Val Val Leu Leu Ala Val Ala Ala Cys
                165                 170                 175

GTC CTC CTC CTG ACC TCG GCC CAG CTT GGA CTG CAC ATC TGG CAG CTG     576
Val Leu Leu Leu Thr Ser Ala Gln Leu Gly Leu His Ile Trp Gln Leu
            180                 185                 190

AGG AGT CAG TGC ATG TGG CCC CGA GAG ACC CAG CTG CTG CTG GAG GTG     624
Arg Ser Gln Cys Met Trp Pro Arg Glu Thr Gln Leu Leu Leu Glu Val
        195                 200                 205

CCG CCG TCG ACC GAA GAC GCC AGA AGC TGC CAG TTC CCC GAG GAA GAG     672
Pro Pro Ser Thr Glu Asp Ala Arg Ser Cys Gln Phe Pro Glu Glu Glu
    210                 215                 220
```

```
CGG GGC GAG CGA TCG GCA GAG GAG AAG GGG CGG CTG GGA GAC CTG TGG      720
Arg Gly Glu Arg Ser Ala Glu Glu Lys Gly Arg Leu Gly Asp Leu Trp
225                 230                 235                 240

GTG TGAGCCTGGC CGTCCTCCGG GGCCACCGAC CGCAGCCAGC CCCTCCCCAG            773
Val

GAGCTCCCCA GGCCGCAGGG GCTCTGCGTT CTGCTCTGGG CCGGGCCCTG CTCCCCTGGC    833

AGCAGAAGTG GGTGCAGGAA GGTGGCAGTG ACCAGCGCCC TGGACCATGC AGTTCGGCGG    893

CCGCTCTAAA GGATCCAAGC TTACGTACGC GTGCATGCGA CGTCATAGCT CTTCTATAGT    953

GTCACCTAAA TTCAATTCAC TGGCCGTCGT TTTACAACGT CCTGACTGGG AAA          1006
```

(2) INFORMATION FOR SEQ ID NO:4:

(i) SEQUENCE CHARACTERISTICS:
        (A) LENGTH: 241 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
                20                  25                  30

Gly Cys Gly Pro Gly Arg Leu Leu Leu Gly Thr Gly Thr Asp Ala Arg
            35                  40                  45

Cys Cys Arg Val His Thr Thr Arg Cys Cys Arg Asp Tyr Pro Gly Glu
        50                  55                  60

Glu Cys Cys Ser Glu Trp Asp Cys Met Cys Val Gln Pro Glu Phe His
65                  70                  75                  80

Cys Gly Asp Pro Cys Cys Thr Thr Cys Arg His His Pro Cys Pro Pro
                85                  90                  95

Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
        115                 120                 125

Lys Pro Trp Thr Asp Cys Thr Gln Phe Gly Phe Leu Thr Val Phe Pro
    130                 135                 140

Gly Asn Lys Thr His Asn Ala Val Cys Val Pro Gly Ser Pro Pro Ala
145                 150                 155                 160

Glu Pro Leu Gly Trp Leu Thr Val Val Leu Leu Ala Val Ala Ala Cys
                165                 170                 175

Val Leu Leu Leu Thr Ser Ala Gln Leu Gly Leu His Ile Trp Gln Leu
            180                 185                 190

Arg Ser Gln Cys Met Trp Pro Arg Glu Thr Gln Leu Leu Leu Glu Val
        195                 200                 205

Pro Pro Ser Thr Glu Asp Ala Arg Ser Cys Gln Phe Pro Glu Glu Glu
    210                 215                 220

Arg Gly Glu Arg Ser Ala Glu Glu Lys Gly Arg Leu Gly Asp Leu Trp
225                 230                 235                 240

Val
```

(2) INFORMATION FOR SEQ ID NO:5:

(i) SEQUENCE CHARACTERISTICS:

```
       (A) LENGTH: 723 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:5:

ATGGCNCARC AYGGNGCNAT GGGNGCNTTY MGNGCNYTNT GYGGNYTNGC NYTNYTNTGY    60

GCNYTNWSNY TNGGNCARMG NCCNACNGGN GGNCCNGGNT GYGGNCCNGG NMGNYTNYTN   120

YTNGGNACNG GNACNGAYGC NMGNTGYTGY MGNGTNCAYA CNACNMGNTG YTGYMGNGAY   180

TAYCCNGGNG ARGARTGYTG YWSNGARTGG GAYTGYATGT GYGTNCARCC NGARTTYCAY   240

TGYGGNGAYC CNTGYTGYAC NACNTGYMGN CAYCAYCCNT GYCCNCCNGG NCARGGNGTN   300

CARWSNCARG GNAARTTYWS NTTYGGNTTY CARTGYATHG AYTGYGCNWS NGGNACNTTY   360

WSNGGNGGNC AYGARGGNCA YTGYAARCCN TGGACNGAYT GYACNCARTT YGGNTTYYTN   420

ACNGTNTTYC CNGGNAAYAA RACNCAYAAY GCNGTNTGYG TNCCNGGNWS NCCNCCNGCN   480

GARCCNYTNG GNTGGYTNAC NGTNGTNYTN YTNGCNGTNG CNGCNTGYGT NYTNYTNYTN   540

ACNWSNGCNC ARYTNGGNYT NCAYATHTGG CARYTNMGNW SNCARTGYAT GTGGCCNMGN   600

GARACNCARY TNYTNYTNGA RGTNCCNCCN WSNACNGARG AYGCNMGNWS NTGYCARTTY   660

CCNGARGARG ARMGNGGNGA RMGNWSNGCN GARGARAARG GNMGNYTNGG NGAYYTNTGG   720

GTN                                                                 723

(2) INFORMATION FOR SEQ ID NO:6:

(i) SEQUENCE CHARACTERISTICS:
       (A) LENGTH: 228 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:6:

Met Gly Ala Phe Arg Ala Leu Cys Gly Leu Ala Leu Leu Cys Ala Leu
1               5                   10                  15

Ser Leu Gly Gln Arg Pro Thr Gly Pro Gly Cys Gly Pro Gly Arg
            20                  25                  30

Leu Leu Leu Gly Thr Gly Thr Asp Ala Arg Cys Cys Arg Val His Thr
            35                  40                  45

Thr Arg Cys Cys Arg Asp Tyr Pro Gly Glu Glu Cys Cys Ser Glu Trp
    50                  55                  60

Asp Cys Met Cys Val Gln Pro Glu Phe His Cys Gly Asp Pro Cys Cys
65                  70                  75                  80

Thr Thr Cys Arg His His Pro Cys Pro Pro Gly Gln Gly Val Gln Ser
                85                  90                  95

Gln Gly Lys Phe Ser Phe Gly Phe Gln Cys Ile Asp Cys Ala Ser Gly
            100                 105                 110

Thr Phe Ser Gly Gly His Glu Gly His Cys Lys Pro Trp Thr Asp Cys
            115                 120                 125

Thr Gln Phe Gly Phe Leu Thr Val Phe Pro Gly Asn Lys Thr His Asn
        130                 135                 140

Ala Val Cys Val Pro Gly Ser Pro Pro Ala Glu Pro Leu Gly Trp Leu
145                 150                 155                 160

Thr Val Val Leu Leu Ala Val Ala Ala Cys Val Leu Leu Leu Thr Ser
```

-continued

```
                165                 170                 175
Ala Gln Leu Gly Leu His Ile Trp Gln Leu Arg Lys Thr Gln Leu Leu
            180                 185                 190

Leu Glu Val Pro Pro Ser Thr Glu Asp Ala Arg Ser Cys Gln Phe Pro
        195                 200                 205

Glu Glu Glu Arg Gly Glu Arg Ser Ala Glu Lys Gly Arg Leu Gly
    210                 215                 220

Asp Leu Trp Val
225
```

(2) INFORMATION FOR SEQ ID NO:7:

(i) SEQUENCE CHARACTERISTICS:
        (A) LENGTH: 232 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Met Gly Ala Phe Arg Ala Leu Cys Gly Leu Ala Leu Leu Cys Ala Leu
1               5                   10                  15

Ser Leu Gly Gln Arg Pro Thr Gly Gly Pro Gly Cys Gly Pro Gly Arg
            20                  25                  30

Leu Leu Leu Gly Thr Gly Thr Asp Ala Arg Cys Cys Arg Val His Thr
        35                  40                  45

Thr Arg Cys Cys Arg Asp Tyr Pro Gly Glu Glu Cys Cys Ser Glu Trp
    50                  55                  60

Asp Cys Met Cys Val Gln Pro Glu Phe His Cys Gly Asp Pro Cys Cys
65                  70                  75                  80

Thr Thr Cys Arg His His Pro Cys Pro Pro Gly Gln Gly Val Gln Ser
                85                  90                  95

Gln Gly Lys Ser Trp Arg Cys Leu Trp Glu Ser Thr Gln Ala Arg Gly
            100                 105                 110

Ser Thr Arg Ala Arg Gly Arg Ala Arg Gly His Arg Cys Pro Ala Arg
        115                 120                 125

Thr Cys Gly Val Trp Gly Pro Glu Ser Cys Glu Ala Gly Gln Ala Arg
    130                 135                 140

Pro Cys Ser Gly Thr Thr Gly His Glu Ala Leu Gly Val Ser Cys Pro
145                 150                 155                 160

Cys Phe Leu Ser Leu Gly Phe Ser Ile Gln His Glu Gly Cys Glu Asn
                165                 170                 175

Pro Ala Gly Arg Trp Gly Arg Val Pro Gly Ala Val Trp Leu Ser Gly
            180                 185                 190

Pro Gly His Pro Ser Cys Leu Ser Pro His Thr Glu Arg Ala Cys
        195                 200                 205

Pro Val Pro Pro Gly Val Leu Ser Gly Ala Trp Gly Cys Thr Leu Phe
    210                 215                 220

Trp Lys Glu Gln Leu Lys Ser Ser
225                 230
```

(2) INFORMATION FOR SEQ ID NO:8:

(i) SEQUENCE CHARACTERISTICS:
        (A) LENGTH: 311 amino acids
        (B) TYPE: amino acid
        (C) STRANDEDNESS: single -continued

```
        (D) TOPOLOGY: linear (ii) MOLECULE TYPE: peptide (xi) SEQUENCE DESCRIPTION: SEQ ID NO:8:

Met Gly Ala Phe Arg Ala Leu Cys Gly Leu Ala Leu Leu Cys Ala Leu
1               5                  10                  15

Ser Leu Gly Gln Arg Pro Thr Gly Gly Pro Gly Cys Gly Pro Gly Arg
            20                  25                  30

Leu Leu Leu Gly Thr Gly Thr Asp Ala Arg Cys Cys Arg Val His Thr
            35                  40                  45

Thr Arg Cys Cys Arg Asp Tyr Pro Gly Glu Glu Cys Cys Ser Glu Trp
50                      55                  60

Asp Cys Met Cys Val Gln Pro Glu Phe His Cys Gly Asp Pro Cys Cys
65                  70                  75                  80

Thr Thr Cys Arg His His Pro Cys Pro Pro Gly Gln Gly Val Gln Ser
                85                  90                  95

Gln Gly Lys Phe Ser Phe Gly Phe Gln Cys Ile Asp Cys Ala Ser Gly
                100                 105                 110

Thr Phe Ser Gly Gly His Glu Gly His Cys Lys Pro Trp Thr Asp Cys
            115                 120                 125

Thr Gln Phe Gly Phe Leu Thr Val Phe Pro Gly Asn Lys Thr His Asn
            130                 135                 140

Ala Val Cys Val Pro Gly Ser Pro Pro Ala Glu Pro Leu Gly Trp Leu
145                 150                 155                 160

Thr Val Val Leu Leu Ala Val Ala Ala Cys Val Leu Leu Leu Thr Ser
                165                 170                 175

Ala Gln Leu Gly Leu His Ile Trp Gln Leu Arg Ser Gln Cys Met Trp
            180                 185                 190

Pro Arg Gly Leu Ser Gln Pro Gly Ala Gly Arg Trp Glu His Gly Cys
            195                 200                 205

Leu Leu Thr Val Ala Pro Leu Gln Arg Pro Ser Cys Cys Trp Arg Cys
            210                 215                 220

Arg Arg Arg Pro Lys Thr Pro Glu Ala Ala Ser Ser Pro Arg Lys Ser
225                 230                 235                 240

Gly Ala Ser Asp Arg Gln Arg Arg Arg Gly Gly Trp Glu Thr Cys Gly
                245                 250                 255

Cys Glu Pro Gly Arg Pro Pro Gly Pro Pro Thr Ala Ala Ser Pro Ser
            260                 265                 270

Pro Gly Ala Pro Gln Ala Ala Gly Ala Leu Arg Ser Ala Leu Gly Arg
            275                 280                 285

Ala Leu Leu Pro Trp Gln Gln Lys Trp Val Gln Glu Gly Gly Ser Asp
            290                 295                 300

Gln Arg Pro Gly Pro Cys Ser
305                 310
```

MAMMALIAN CELL SURFACE ANTIGENS; RELATED REAGENTS

The present filing is a conversion from U.S. Provisional Patent Applications No. 60/023,419, filed Aug. 16, 1996 and 60/027,901, filed Oct. 7, 1996, to a U.S. Utility Patent Application.

FIELD OF THE INVENTION

The present invention generally pertains to molecules that control activation and expansion of mammalian cells, especially mammalian immune system cells. The invention provides purified genes, proteins, antibodies, and related reagents useful, for example, to regulate activation, development, differentiation, and function of various cell types, including hematopoietic cells. In particular, the invention provides mammalian 312C2 genes, gene products, compositions, and methods for using these.

BACKGROUND OF THE INVENTION

The activation of resting T cells is critical to most immune responses and allows these cells to exert their regulatory or effector capabilities. See Paul (ed; 1993) *Fundamental Immunology* 3d ed., Raven Press, N.Y. Increased adhesion between T cells and antigen presenting cells (APC) or other forms of primary stimuli, e.g., immobilized monoclonal antibodies (mAb), can potentiate the T-cell receptor signals. T-cell activation and T cell expansion depends upon engagement of the T-cell receptor (TCR) and co-stimulatory signals provided by accessory cells. See, e.g., Jenkins and Johnson (1993) *Curr. Opin. Immunol.* 5:361–367; Bierer and Hahn (1993) *Semin. Immunol.* 5:249–261; June, et al. (1990) *Immunol. Today* 11:211–216; and Jenkins (1994) *Immunity* 1:443–446. A major, and well-studied, co-stimulatory interaction for T cells involves either CD28 or CTLA-4 on T cells with either B7 or B70 (Jenkins (1994) *Immunity* 1:443–446). Recent studies on CD28 deficient mice (Shahinian, et al. (1993) *Science* 261:609–612; Green, et al. (1994) *Immunity* 1:501–508) and CTLA-4 immunoglobulin expressing transgenic mice (Ronchese, et al. (1994) *J. Exp. Med.* 179:809–817) have revealed deficiencies in some T-cell responses though these mice have normal primary immune responses and normal CTL responses to lymphocytic chorimeningitis virus and vesicular stomatitis virus. As a result, both these studies conclude that other co-stimulatory molecules must be supporting T-cell function. However, identification of these molecules which mediate distinct costimulatory signals has been difficult.

The inability to modulate activation signals prevents control of inappropriate developmental or physiological responses in the immune system. The present invention provides at least one alternative costimulatory molecule, agonists and antagonists of which will be useful in modulating a plethora of immune responses.

SUMMARY OF THE INVENTION

The present invention is based, in part, upon the discovery of a family of proteins which appear to act as a costimulator of T cell activation. In particular, the invention provides mammalian, e.g., rodent and primate, genes designated m312C2 and h312C2, respectively, which are expressed in the thymus, and are induced on T cells and spleen cells following activation. Engagement of 312C2 appears stimulate proliferation of T cell clones, antigen-specific proliferation and cytokine production by T cells, and appears to potentiate T cell expansion or apoptosis. The mouse and human embodiments are described in greater detail, but the invention encompasses related mammalian genes, proteins, antibodies, and uses thereof. Functional equivalents exhibiting significant sequence homology are available from other mammalian and non-mammalian species. Moreover, the ligand of 312C2 can function as its binding partner to stimulate other cells expressing the antigen.

The present invention provides a substantially pure or recombinant 312C2 protein or peptide fragment thereof. The protein or polypeptide is expressed, e.g., activated T cells or specifically binds to antibodies generated against SEQ ID NO: 2 or 4. Some embodiments involve a protein or peptide selected from a protein or peptide from a warm blooded animal selected from the group of birds and mammals, including a rodent or primate. The groups further consist of a protein or peptide which comprises at least one polypeptide segment of SEQ ID NO: 2 or 4; is not glycosylated; is in a buffered solulation; is attached to a solid substrate; exhibits a plurality of epitopes from SEQ ID NO: 2 or 4; is synthetically labeled; is conjugated to a chemical moiety; is a 5-fold or less substitution from a natural sequence; or is a deletion or insertion variant from a natural sequence. The protein or peptide can comprise a sequence from the extracellular or the intracellular portion of a 312C2; or be a fusion protein.

The invention also provides a recombinant nucleic acid comprising sequence at least about 70% identity over a stretch of at least about 30 nucleotides to a 312C2 nucleic acid sequence of SEQ ID NO: 1, 3 or 5, useful, e.g., as a probe or PCR primer for a related gene. Another embodiment further encodes a polypeptide sharing a plurality of specific epitopes and comprising at least about 60% identity over a stretch of at least about 20 amino acids to a 312C2 sequence of SEQ ID NO: 2 or 4.

Another embodiment is a sterile composition comprising a 312C2 protein and a pharmaceutically acceptable carrier. Other compositions may combine said entities with an agonist or antagonist of other T cell signaling molecules, e.g., signaling entities through the T cell receptor, CD40, CD40 ligand, CTLA-8, CD28, B7, B70, BAS-1, SLAM, etc.

The invention also embraces an antibody which specifically binds a 312C2 protein or peptide, e.g., wherein the 312C2 is a mammalian protein, including a mouse; the antibody is raised against a purified 312C2 peptide sequence of SEQ ID NO: 2 or 4; the antibody is a monoclonal antibody; the antibody is detectably labeled; the antibody is attached to a solid substrate; or the antibody is in a sterile or buffered composition. The antibodies also make available a method of purifying a 312C2 protein or peptide from other materials in a mixture comprising contacting the mixture to an anti-312C2 antibody, and separating bound 312C2 from other materials.

Another aspect of the invention is an isolated or recombinant nucleic acid capable of encoding a 312C2 protein or peptide, including a nucleic acid which encodes a mature polypeptide sequence of SEQ ID NO: 2 or 4; which includes a sequence of SEQ ID NO: 1, 3 or 5; which encodes a sequence from an extracellular domain of a natural 312C2; which encodes a sequence from an intracellular domain of a natural 312C2; which is detectably labeled; which is attached to a solid substrate; or is in a sterile composition. Such nucleic acid embodiments also include an expression or replicating vector.

Also provided is a method of expressing a 312C2 peptide by expressing a nucleic acid encoding a 312C2 polypeptide. The invention also provides a cell, tissue, organ, or organism comprising a nucleic acid encoding a 312C2 peptide.

The invention also provides a kit containing a substantially pure 312C2 or fragment; an antibody or receptor which specifically binds a 312C2; or a nucleic acid, or its complement, encoding a 312C2 or peptide. This kit also provides methods for detecting in a sample the presence of a nucleic acid, protein, or antibody, comprising testing said sample with such a kit.

The invention also supplies methods of modulating the physiology of a cell comprising contacting said cell with a substantially pure 312C2 or a fragment thereof; or with an antibody or ligand which specifically binds a 312C2; or with a nucleic acid encoding a 312C2 or a peptide fragment thereof. Certain preferred embodiments include a method where the cell is a T cell and the modulating of physiology is activation of the T cell or apoptosis of the T cell; or where the cell is in a tissue and/or in an organism.

The invention further provides a method of treating a patient having an abnormal immune response by administering an effective dose of an antibody or binding partner specific for 312C2; a 312C2 protein or polypeptide; or a nucleic acid encoding a 312C2 peptide. The abnormal immune response is characterized by a T cell immune deficiency; chronic inflammation; or tissue rejection.

DETAILED DESCRIPTION OF THE PREFERRED EMBODIMENTS

I. Definitions

The terms "nucleic acid" "probe", or "primer" include reference to a deoxyribonucleotide, ribonucleotide, or mixed polymer in either single- or double-stranded form, and unless otherwise limited, encompasses known analogs of natural polynucleotides that hybridize to nucleic acids in manner similar to naturally occurring polynucleotides. Unless otherwise indicated, a particular nucleic acid sequence includes the perfect complementary sequence thereof. Eukaryotic nucleic acids are nucleic acids from eukaryotic cells, preferably cells of multicellular eukaryotes.

Unless otherwise indicated, nucleic acids are written left to right in 5' to 3' orientation; amino acid sequences are written left to right in amino to carboxy orientation, respectively. Numeric ranges are inclusive of the numbers defining the range. The terms defined below are more fully defined by reference to the Specification as a whole.

The term "recombinant" when used with reference to a cell, or nucleic acid, or vector, includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (nonrecombinant) form of the cell or express native genes that are otherwise abnormally expressed, under expressed, or not expressed at all.

The term "subsequence" in the context of a referenced nucleic acid sequence includes reference to a contiguous sequence from the nucleic acid having fewer nucleotides in length than the referenced nucleic acid. In the context of a referenced protein, polypeptide, or peptide sequence (collectively, "protein"), "subsequence" refers to a contiguous sequence from the referenced protein having fewer amino acids than the referenced protein. The terminus of such subsequences include all combinations consistent with a defined length.

Amino acids may be referred to herein by either their commonly known three letter symbols or by the one-letter symbols recommended by the IUPAC-IuB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations", which are one species of conservatively modified variations. Every nucleic acid sequence herein which encodes a polypeptide also describes equivalents which encompass every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence. Substitutions with functionally equivalent unusual nucleotides or analogs are intended, e.g., inositol, etc.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Iethionine (M), Valine (V); and
6) Phenylalanine (F), Tyrosine (Y), Tryptophan (W). See also, Creighton (1984) *Proteins* W.H. Freeman and Company.

By "contiguous amino acids from" in the context of a specified number of amino acid residues from a specified sequence, is meant a sequence of amino acids of the specified number from within the specified reference sequence which has the identical order of amino acids each of which is directly adjacent to the same amino acids as in the reference sequence.

The term "polypeptide" as used herein includes a significant fragment or segment, and encompasses a stretch of amino acid residues of at least about 8 amino acids, generally at least about 12 amino acids, typically at least about 16 amino acids, preferably at least about 20 amino acids, and, in particularly preferred embodiments, at least about 30 or more amino acids, e.g., 40, 50, 60, 70, 80, 100, etc. The ends may be are virtually all combinations consistent with length.

The term "plurality of non-overlapping fragments" encompasses a series of polypeptide fragments or segments. A plurality includes 2, 3, 4, 5, etc., polypeptide fragments.

The terms "biologically pure" or "isolated" refer to material which is substantially or essentially free from components which normally accompany or interact with it as found in its naturally occurring environment. The isolated material optionally comprises material not found with the material in its natural environment.

The phrase "encodes a protein" in the context of nucleic acids includes those nucleic acids encoding naturally occurring proteins or derivatives of natural proteins, but which are deliberately modified or engineered to no longer hybridize to a natural gene encoding the protein of natural origin under the stated conditions.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison may be conducted by the local homology algorithm of Smith and Waterman (1981) *Adv. Appl. Math.* 2:482; by the homology alignment algorithm of Needleman and Wunsch (1970) *J. Mol. Biol.* 48:443–445; by the search for similarity method of Pearson and Lipman (1988) *Proc. Natl. Acad. Sci. USA* 85:2444; by computerized implementations of these algorithms (including, but not limited to CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 575 Science Dr., Madison, Wis., USA); the CLUSTAL program is well described by Higgins and Sharp (1988) *Gene* 73:237–244 and Higgins and Sharp (1989) *CABIOS* 5:151–153; Corpet, et al. (1988) *Nucleic Acids Research* 16:10881–90; Huang, et al. (1992) *Computer Applications in the Biosciences* 8:155–65, and Pearson, et al. (1994) *Methods in Molecular Biology* 24:307–31. Alignment is also often performed by inspection and manual alignment.

The terms "identical" or "sequence identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller (1988) *Computer Applic. Biol. Sci.* 4:11–17, e.g., as implemented in the program PC/GENE (Intelligenetics, Mountain View, Calif., USA).

The terms "substantial identity" or "similarity" of polynucleotide sequences means that a polynucleotide comprises a sequence that has at least 60% sequence identity, preferably at least 80%, more preferably at least 90%, and most preferably at least 95%, compared to a reference sequence using, e.g., the programs described above (preferably BLAST) using standard parameters. One indication that two nucleic acid sequences are substantially identical is that the polypeptide which the first nucleic acid encodes is immunologically cross reactive with the polypeptide encoded by the second nucleic acid.

Another indication that two nucleic acid sequences have substantial identity is that the two molecules hybridize to each other under "moderate stringency hybridization conditions" (or "moderate conditions") or better. Exemplary "moderate stringency hybridization conditions" include a hybridization in a buffer of 40% formamide, 1 M NaCl, 1% SDS at 37° C., and a wash in 1× SSC at 45° C. A positive hybridization is at least twice background. Those of ordinary skill will readily recognize that alternative hybridization and wash conditions can be utilized to provide conditions of similar or higher stringency. Nucleic acids which do not hybridize to each other under moderate stringency hybridization conditions are still substantially identical if the polypeptides which they encode are substantially identical. This occurs, e.g., when a copy of a nucleic acid is created, e.g., using the maximum codon degeneracy permitted by the genetic code.

The terms "substantial identity" or "similarity" in the context of a peptide indicates that a peptide comprises a sequence with at least 60% sequence identity to a reference sequence, usually at least 70%, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443. An indication that two peptide sequences are substantially identical is that one peptide is immunologically reactive with antibodies raised against the second peptide. Thus, a peptide is substantially identical to a second peptide, for example, where the two peptides differ only by a conservative substitution. Generally, similarity is determined using a comparison window having a length of any number from 20 contiguous positions at various positions in the respective molecules to the number of residues in the full-length core region sequence, where the comparison window is within the core sequence.

The terms "oligonucleotide" or "polynucleotide" probes include reference to both double stranded and single stranded DNA or RNA. The terms also refer to synthetically or recombinantly derived sequences essentially free of non-nucleic acid contamination.

As used herein, "contact" or "contacting" means to place in direct physical association, e.g., mixing of solutions.

"Biological sample" as used herein is a sample of biological tissue or fluid that contains, or is being tested for presence of, 312C2 protein, or another of described composition, e.g., nucleic acid or protein. Such samples include, but are not limited to, sputum, amniotic fluid, blood, blood cells, e.g., white cells, or tissue, e.g., spleen, thymus, bone marrow, or lymph node. Biological samples may also include sections of tissues such as frozen sections taken for histological purposes. Examples of biological samples include a cell sample from nervous, muscular, glandular or epithelial tissue or from the immune system (e.g., T cells). A biological sample is typically obtained from a eukaryotic organism, preferably a multicellular eukaryotes such as insect, protozoa, birds, fish, reptiles, and preferably a mammal such as rat, mice, cow, dog, guinea pig, pig, goat, or rabbit, and most preferably a primate such as macaques, chimpanzees, or humans.

An "expression vector" is a nucleic acid construct, typically generated recombinantly or synthetically, with a series of specified nucleic acid elements which permit transcription of a particular nucleic acid in a host cell. The expression vector can be part of a plasmid, virus, or nucleic acid fragment. Typically, the expression vector includes a nucleic acid to be transcribed, and a promoter.

The phrase "functional effects" in the context of assays for testing compounds affecting the 312C2 includes the determination of any parameter that is indirectly or directly under the influence of the 312C2. It includes changes such as increases or decreases of transcription or second messenger or lymphokine release.

By "selectively hybridizing" or "selective hybridization" or "selectively hybridizes" is meant hybridization, under stringent hybridization conditions, of a nucleic acid sequence to a specified nucleic acid target sequence to a detectably greater degree than its hybridization to non-target nucleic acid sequences and/or to the substantial exclusion of non-target nucleic acids. Selectively hybridizing sequences typically have at least 80% sequence identity, usually 90% sequence identity, preferably 95% identity, more preferably 98% identity, and most preferably 100% sequence identity (i.e., complementary) with each other over lengths which typically start from about 10 nucleotides, e.g., 13, 17, 20, 23, 26, 29, 32, etc. "Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "stringent conditions" or "stringent hybridization conditions" refer to conditions under which a probe will hybridize to its target sequence, to a detectably greater degree than other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The $T_m$ is the temperature (under defined ionic strength and pH) at which 50% of a complementary target sequence hybridizes to a perfectly matched probe. Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30% formamide, 1 M NaCl, 1% SDS at 37° C., and a wash in 2× SSC at 50° C. Exemplary high stringency conditions include hybridization in 50% formamide, 1 M NaCl, 1% SDS at 37° C., and a wash in 0.1× SSC at 60° C.

"Stringent hybridization conditions" or "stringent conditions" in the context of nucleic acid hybridization assay formats are sequence dependent, and are different under different environmental parameters. An extensive guide to the hybridization of nucleic acids is found e.g., in Tijssen (1993) *Laboratory Techniques in Biochemistry and Molecular Biology—Hybridization with Nucleic Acid Probes* Part I, Chapter 2 "Overview of principles of hybridization and the strategy of nucleic acid probe assays", Elsevier, New York. Stringent conditions are sequence-dependent and will be different in different circumstances. Longer sequences hybridize specifically at higher temperatures.

By "hybridization complex" is meant a duplex nucleic acid sequence formed by selective hybridization of two single-stranded nucleic acid sequences with each other.

By "host cell" is meant a cell which is manipulated to contain and, in certain instances, express a molecule, usually a nucleic acid. Host cells may be prokaryotic cells such as *E. coli*, or eukaryotic cells such as yeast, insect, amphibian, or mammalian cells.

The term "antibody" also includes antigen binding forms of antibodies (e.g., Fab, F(ab)$_2$). The term "antibody" refers to a polypeptide substantially encoded by an immunoglobulin gene or immunoglobulin genes, or fragments thereof which specifically bind and recognize an analyte (antigen). Antibodies exist, e.g., as intact immunoglobulins or as a number of well characterized fragments e.g., produced by digestion with various peptidases. Thus, for example, pepsin digests an antibody below the disulfide linkages in the hinge region to produce F(ab)'$_2$, a dimer of Fab which itself is a light chain joined to $V_H$–$C_H1$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region, see, e.g., Paul (ed.) (1993) *Fundamental Immunology*, 3rd ed., Raven Press, N.Y. While various antibody fragments are defined in terms of the digestion of an intact antibody, one of skill will appreciate that such fragments may be synthesized de novo either chemically or by utilizing recombinant DNA methodology. Thus, the term antibody, as used herein, is often functionally equivalent to antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

By "immunologically reactive conditions" is meant conditions which allow an antibody, generated to a particular epitope, to bind to that epitope to a detectably greater degree than the antibody binds to substantially all other epitopes. Immunologically reactive conditions are dependent upon the format of the antibody binding reaction and, typically are those utilized in immunoassay protocols. See Harlow and Lane (1988) *Antibodies: A Laboratory Manual*, Cold Spring Harbor Publications, New York, for a description of immunoassay formats and conditions.

By "antibody reactive to a protein" is meant the protein is "specifically irnmunoreactive with an antibody."

The phrase "specifically immunoreactive with an antibody", or "specifically binds to an antibody" when referring to a protein or peptide, refers to a binding reaction between an antibody and a protein having an epitope recognized by the antigen binding site of the antibody. This binding reaction is determinative of the presence of a protein having the recognized epitope amongst the presence of a heterogeneous population of proteins and other biologics. Thus, under designated immunoassay conditions, the specified antibodies bind to a protein having the recognized epitope and bind, if at all, to a detectably lesser degree to other proteins lacking the epitope which are present in the sample.

Specific binding to an antibody under such conditions may require an antibody that is selected for its specificity for a particular protein. For example, antibodies raised to the 312C2 of SEQ ID NO: 2 or 4 can be selected from to obtain antibodies specifically immunoreactive with that particular protein and not with other proteins. The proteins used as immunogens can be in native conformation or denatured, e.g., so as to provide a linear epitope. Preferably, antibody preparations which specifically recognize multiple epitopes will be used.

A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

By "antigen" is meant a substance to which an antibody can be generated and/or to which the antibody is specifically immunoreactive with. An antibody immunologically reactive with a particular antigen can be generated in vivo or by recombinant methods such as selection of libraries of recombinant antibodies in phage or similar vectors. See, e.g., Huse et al. (1989) *Science* 246:1275–1281; and Ward, et al. (1989) *Nature* 341:544–546; and Vaughan et al. (1996) *Nature Biotechnology*, 14:309–314.

By "transfected" is meant the introduction of a nucleic acid into a eukaryotic cell where the nucleic acid may be incorporated into the genome of the cell (i.e., chromosome, plasmid, or mitochondrial DNA), converted into an autonomous replicon, or transiently expressed (e.g., transfected mRNA). The transfection can be in vivo or ex vivo. "Ex vivo" means outside the body of the organism from which a cell or cells is obtained or from which a cell line is isolated. Ex vivo transfection is preferably followed by re-infusion of the cells back into the organism. In contrast, by "in vivo" is meant within the body of the organism from which the cell was obtained or from which a cell line is isolated.

The term "binding composition" refers to molecules that bind with specificity to 312C2, e.g., in a cell adhesion pairing type fashion, or an antibody-antigen interaction. It also includes compounds, e.g., proteins, which specifically associate with 312C2, including in a natural physiologically relevant protein-protein interaction, either covalent or non-covalent. The molecule may be a polymer, or chemical reagent. A functional analog may be an antigen with structural modifications, or it may be a molecule which has a molecular shape which interacts with the appropriate binding determinants. The compounds may serve as agonists or antagonists of the binding interaction, see, e.g., Goodman, et al. (eds.) (1990) *Goodman & Gilman's: The Pharmacological Bases of Therapeutics* (8th ed.), Pergamon Press.

Substantially pure typically means that the protein is free from other contaminating proteins, nucleic acids, or other biologicals with which it is associated in the original source organism. Purity may be assayed by standard methods, typically by weight, and will ordinarily be at least about 40% pure, generally at least about 50% pure, often at least about 60% pure, typically at least about 80% pure, preferably at least about 90% pure, and in most preferred embodiments, at least about 95% pure. Carriers or excipients will often be added, or aqueous buffers or organic solvents used in certain situations.

II. General

The present invention provides amino acid sequences and DNA sequences encoding various mammalian proteins which are antigens found in the early stages of T cell activation, e.g., which can activate a T cell. Among these proteins are antigens which modulate, e.g., induce or prevent proliferation or differentiation of T cells, among other physiological effects. The full length antigens, and fragments, or antagonists will be useful in physiological modulation of cells expressing the antigen. The proteins will also be useful as antigens, e.g., immunogens, for raising antibodies to various epitopes on the protein, both linear and conformational epitopes. The molecule may be useful in defining or isolating functional T cell or NK cell subsets.

A cDNA encoding mouse 312C2 was isolated from an activated pro T-cell cDNA library, see Kelner, et al. (1994) *Science* 266:13995–1399. The mouse 312C2 cDNA contains a stretch of about 1073 bp in length and contained one large open reading frame encoding a type I transmembrane protein. Structural features include an N-terminal leader sequence of about 19 amino acids, an extracellular region of about 153 amino acids, a hydrophobic presumptive membrane spanning portion of about 25 amino acids, and a presumptive cytoplasmic domain of about 50 amino acids. See SEQ ID NO: 2. A human cDNA was isolated using the mouse clone to probe a human anergic T cell library designated HY06. See SEQ ID NO: 3 and 4. A transmembrane region may begin at about amino acid 155 and end at about amino acid 185 based on hydrophobicity analysis. The rodent and primate sequences can be aligned.

312C2 exhibits structural motifs characteristic of a member of the TNF receptor family, with numerous cysteine repeats. Compare, e.g., with the CD40, OX40, TNF receptor, NGF receptor, and FASL receptor. The intracellular portion 312C2 does not contain a death domain as described, e.g., in Pan, et al. (1997) *Science* 277:815–818; and Sheridan, et al. (1997) *Science* 277:818–821. Lack of the death domain motif may indicate that 312C2 is likely to work in the control of proliferation rather than apoptosis.

As used herein, the term "mouse 312C2" shall encompass, when used in a protein context, a protein having amino acid sequence shown in SEQ ID NO: 2, or a significant fragment of such a protein, or another highly homologous protein derived from mouse. The term "human 312C2" shall encompass, when used in a protein context, a protein having amino acid sequence shown in SEQ ID NO: 4, or a significant fragment of such a protein, or another highly homologous protein derived from human.

The natural antigens are capable of mediating various biochemical responses which lead to biological or physiological responses in target cells. The embodiments characterized herein are from mouse and human, but other species and tissue specific variants exist. Additional sequences for proteins in other mammalian species, e.g., primates and rodents, should also be available. See below. The descriptions below are directed, for exemplary purposes, to a mouse or human 312C2, but are likewise applicable to related embodiments from other species.

III. Purified 312C2

The mouse 312C2 nucleic acid sequence is shown in SEQ ID NO: 1, and the amino acid sequence is shown in SEQ ID NO: 2, the human 312C2 nucleic acid sequence is shown in SEQ ID NO: 3, and the corresponding amino acid sequence is shown in SEQ ID NO: 4. A reverse translation of the human 312C2 sequence is shown in SEQ ID NO: 5. These amino acid sequences, provided amino to carboxy, are important in providing sequence information about the antigen allowing for distinguishing the protein from other proteins and exemplifying numerous variants. Moreover, the peptide sequences allow preparation of peptides to generate antibodies to recognize such segments, and nucleotide sequences allow preparation of oligonucleotide probes, both of which are strategies for detection or isolation, e.g., cloning, of genes encoding such sequences.

The mouse 312C2 nucleotide and predicted amino-acid sequence, particularly the predicted leader sequence runs from about Met1 through Gly19, though natural boundaries may be different, also depending upon cell type. A polyadenylation signal occurs at nucleotide position 1010. The poly A tail begins at position 1034. See SEQ ID NO: 1 and 2. The transmembrane domain is predicted to encompass amino acids beginning at about 154 through about 179.

In human the putative leader sequence runs from about Met1 through about Leu18. The transmembrane domain is predicted to begin at out amino acid 153 through about 182. Again the natural boundaries may vary.

Antibodies to these proteins typically bind to a 312C2 with high affinity, e.g., at least about 100 nM, usually better than about 30 nM, preferably better than about 10 nM, and more preferably at better than about 3 nM. Homologous proteins would be found in mammalian species other than mouse, e.g., primates or rodents. Non-mammalian species should also possess structurally or functionally related genes and proteins, e.g., birds or amphibians.

Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. For diagnostic purposes, the temperature will usually be about room temperature or warmer, but less than the denaturation temperature of components in the assay. For therapeutic purposes, the temperature will usually be body temperature, typically about 37° C. for humans and mice, though under certain situations the temperature may be raised or lowered in situ or in vitro.

The size and structure of the polypeptide should generally be in a substantially stable state, and usually not in a denatured state. The polypeptide may be associated with other polypeptides in a quaternary structure, e.g., to confer solubility, or associated with lipids or detergents in a manner which approximates natural lipid bilayer interactions. In certain contexts, e.g., Western blots, the protein will be denatured, and/or attached to a solid substrate, e.g., in an affinity column.

The solvent and electrolytes will usually be a biologically compatible buffer, of a type used for preservation of biological activities, and will usually approximate a physiological aqueous solvent. Usually the solvent will have a neutral pH, typically between about 5 and 10, and preferably about 7.5. On some occasions, one or more detergents will be added, typically a mild non-denaturing one, e.g., CHS (cholesteryl hemisuccinate) or CHAPS (3-[3-cholamidopropyl)dimethylammonio]-1-propane sulfonate), or a low enough concentration as to avoid significant disruption of structural or physiological properties of the protein.

A. Physical Variants

This invention also encompasses proteins or peptides having substantial amino acid sequence identity with the amino acid sequence of the 312C2. The variants include species, polymorphic, or allelic variants.

Amino acid sequence homology, or sequence identity, is determined by optimizing residue matches, if necessary, by introducing gaps as required. See also Needleham, et al. (1970) *J. Mol. Biol.* 48:443–453; Sankoff, et al. (1983) Chapter One in *Time Warps, String Edits, and Macromolecules: The Theory and Practice of Sequence Comparison*, Addison-Wesley, Reading, Mass.; and software packages from IntelliGenetics, Mountain View, Calif.; and the University of Wisconsin Genetics Computer Group, Madison, Wis. Sequence identity changes when considering conservative substitutions as matches. Conservative substitutions typically include substitutions within the following groups: glycine, alanine, valine, isoleucine, leucine; aspartic acid, glutamic acid; asparagine, glutamine; serine, threonine; lysine, arginine; and phenylalanine, tyrosine. Homologous amino acid sequences are typically intended to include natural polymorphic or allelic and interspecies variations in each respective protein sequence. Typical homologous proteins or peptides will have from 25–100% identity (if gaps can be introduced), to 50–100% identity (if conservative substitutions are included) with the amino acid sequence of the 312C2. Identity measures will be at least about 35%, generally at least about 40%, often at least about 50%, typically at least about 60%, usually at least about 70%, preferably at least about 80%, and more preferably at least about 90%.

The isolated 312C2 DNA can be readily modified by nucleotide substitutions, nucleotide deletions, nucleotide insertions, and inversions of nucleotide stretches. These modifications result in novel DNA sequences which encode these antigens, their derivatives, or proteins having similar physiological, immunogenic, antigenic, or other functional activity. These modified sequences can be used to produce mutant antigens or to enhance expression. Enhanced expression may involve gene amplification, increased transcription, increased translation, and other mechanisms. "Mutant 312C2" encompasses a polypeptide otherwise falling within the sequence identity definition of the 312C2 as set forth above, but having an amino acid sequence which differs from that of 312C2 as normally found in nature, whether by way of deletion, substitution, or insertion. This generally includes proteins having significant identity with a protein having sequence of SEQ ID NO: 2, and as sharing various biological activities, e.g., antigenic or immunogenic, with those sequences, and in preferred embodiments contain most of the full length disclosed sequences. Preferred variants will share a plurality of immune epitopes with the recited sequences, or equivalent proteins. Full length sequences will typically be preferred, though truncated versions will also be useful, likewise, genes or proteins found from natural sources are typically most desired. Similar concepts apply to different 312C2 proteins, particularly those found in various warm blooded animals, e.g., mammals and birds. These descriptions are generally meant to encompass all 312C2 proteins, not limited to the particular mouse or human embodiments specifically discussed.

312C2 mutagenesis can also be conducted by making amino acid insertions or deletions. Substitutions, deletions, insertions, or any combinations may be generated to arrive at a final construct. Insertions include amino- or carboxyterminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See, e.g., Sambrook, et al. (1989); Ausubel, et al.

(1987 and Supplements); and Kunkel, et al. (1987) *Methods in Enzymol.* 154:367–382.

The present invention also provides recombinant proteins, e.g., heterologous fusion proteins using segments from these proteins. A heterologous fusion protein is a fusion of proteins or segments which are naturally not normally fused in the same manner. A similar concept applies to heterologous nucleic acid sequences.

In addition, new constructs may be made from combining similar functional domains from other proteins. For example, target-binding or other segments may be "swapped" between different new fusion polypeptides or fragments. See, e.g., Cunningham, et al. (1989) *Science* 243:1330–1336; and O'Dowd, et al. (1988) *J. Biol. Chem.* 263:15985–15992.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence, e.g., PCR techniques.

B. Functional Variants

The blocking of physiological response to 312C2s may result from the inhibition of binding of the antigen to its binding partner, e.g., another of itself, likely through competitive inhibition. Thus, in vitro assays of the present invention will often use isolated protein, membranes from cells expressing a membrane associated recombinant 312C2, soluble fragments comprising antigen binding segments of these proteins, or fragments attached to solid phase substrates. These assays will also allow for the diagnostic determination of the effects of either binding segment mutations and modifications, or antigen mutations and modifications, e.g., 312C2 analogs. Structure-activity analysis will be performed with mutational variants.

This invention also contemplates the use of competitive drug screening assays, e.g., where neutralizing antibodies to antigen or binding fragments compete with a test compound for binding to the protein, e.g., of natural protein sequence.

"Derivatives" of 312C2 antigens include amino acid sequence mutants from naturally occurring forms, glycosylation variants, and covalent or aggregate conjugates with other chemical moieties. Covalent derivatives can be prepared by linkage of functionalities to groups which are found in 312C2 amino acid side chains or at the N- or C-termini, e.g., by standard means. See, e.g., Lundblad and Noyes (1988) *Chemical Reagents for Protein Modification*, vols. 1–2, CRC Press, Inc., Boca Raton, Fla.; Hugli (ed.) (1989) *Techniques in Protein Chemistry*, Academic Press, San Diego, Calif.; and Wong (1991) *Chemistry of Protein Conjugation and Cross Linking*, CRC Press, Boca Raton, Fla.

In particular, glycosylation alterations are included, e.g., made by modifying the glycosylation patterns of a polypeptide during its synthesis and processing, or in further processing steps. See, e.g., Elbein (1987) *Ann. Rev. Biochem.* 56:497–534. Also embraced are versions of the peptides with the same primary amino acid sequence which have other minor modifications, including phosphorylated amino acid residues, e.g., phosphotyrosine, phosphoserine, or phosphothreonine.

Fusion polypeptides between 312C2s and other homologous or heterologous proteins are also provided. Many cytokine receptors or other surface proteins are multimeric, e.g., homodimeric entities, and a repeat construct may have various advantages, including lessened susceptibility to proteolytic cleavage. Typical examples are fusions of a reporter polypeptide, e.g., luciferase, with a segment or domain of a protein, e.g., a receptor-binding segment, so that the presence or location of the fused ligand may be easily determined. See, e.g., Dull, et al., U.S. Pat. No. 4,859,609. Other gene fusion partners include bacterial β-galactosidase, trpE, Protein A, β-lactamase, alpha amylase, alcohol dehydrogenase, yeast alpha mating factor, and detection or purification tags such as a FLAG sequence of His6 sequence. See, e.g., Godowski, et al. (1988) *Science* 241:812–816.

Fusion peptides will typically be made by either recombinant nucleic acid methods or by synthetic polypeptide methods. Techniques for nucleic acid manipulation and expression are described generally, e.g., in Sambrook, et al. (1989) *Molecular Cloning: A Laboratory Manual* (2d ed.), vols. 1–3, Cold Spring Harbor Laboratory; and Ausubel, et al. (eds.) (1993) *Current Protocols in Molecular Biology*, Greene and Wiley, New York. Techniques for synthesis of polypeptides are described, e.g., in Merrifield (1963) *J. Amer. Chem. Soc.* 85:2149–2156; Merrifield (1986) *Science* 232:341–347; Atherton, et al. (1989) *Solid Phase Peptide Synthesis: A Practical Approach*, IRL Press, Oxford; and Grant (1992) *Synthetic Peptides: A User's Guide*, W. H. Freeman, New York.

This invention also contemplates the use of derivatives of 312C2s other than variations in amino acid sequence or glycosylation. Such derivatives may involve covalent or aggregative association with chemical moieties. Covalent or aggregative derivatives will be useful as immunogens, as reagents in immunoassays, or in purification methods such as for affinity purification of binding partners, e.g., other antigens. A 312C2 can be immobilized by covalent bonding to a solid support such as cyanogen bromide-activated SEPHAROSE, by methods which are well known in the art, or adsorbed onto polyolefin surfaces, with or without glutaraldehyde cross-linking, for use in the assay or purification of anti-312C2 antibodies or an alternative binding composition. Western blot techniques are also common. The 312C2s can also be labeled with a detectable group, e.g., for use in diagnostic assays. Purification of 312C2 may be effected by an immobilized antibody or complementary binding partner.

A solubilized 312C2 or fragment of this invention can be used as an immunogen for the production of antisera or antibodies specific for binding to the antigen or fragments thereof. Purified antigen can be used to screen or purify monoclonal antibodies or antigen-binding fragments, encompassing antigen binding fragments of natural antibodies, e.g., Fab, Fab', $F(ab)_2$, etc. Purified 312C2s can also be used as a reagent to detect antibodies generated in response to the presence of elevated levels of the antigen or cell fragments containing the antigen, both of which may be diagnostic of an abnormal or specific physiological or disease condition. This invention contemplates antibodies raised against amino acid sequences encoded by nucleotide sequence shown in SEQ ID NO: 1, or fragments of proteins containing it. In particular, this invention contemplates antibodies having binding affinity to or being raised against specific fragments which are predicted to lie outside of the lipid bilayer, both extracellular or intracellular.

The present invention contemplates the isolation of additional closely related species variants. Southern and Northern blot analysis should establish that similar genetic entities exist in other mammals. It is likely that 312C2s are widespread in species variants, e.g., rodents, lagomorphs, carnivores, artiodactyla, perissodactyla, and primates.

The invention also provides means to isolate a group of related antigens displaying both distinctness and similarities in structure, expression, and function. Elucidation of many of the physiological effects of the molecules will be greatly accelerated by the isolation and characterization of additional distinct species variants of them. In particular, the present invention provides useful probes for identifying additional homologous genetic entities in different species.

The isolated genes will allow transformation of cells lacking expression of a corresponding 312C2, e.g., either species types or cells which lack corresponding antigens and exhibit negative background activity. This should allow analysis of the function of 312C2 in comparison to untransformed control cells.

Dissection of critical structural elements which effect the various activation or differentiation functions mediated through these antigens is possible using standard techniques of modern molecular biology, particularly in comparing members of the related class. See, e.g., the homolog-scanning mutagenesis technique described in Cunningham, et al. (1989) Science 243:1339–1336; and approaches used in O'Dowd, et al. (1988) J. Biol. Chem. 263:15985–15992; and Lechleiter, et al. (1990) EMBO J. 9:4381–4390. Structure activity relationship can be analyzed using variants.

Intracellular functions would probably involve segments of the antigen which are normally accessible to the cytosol. However, protein internalization may occur under certain circumstances, and interaction between intracellular components and "extracellular" segments may occur. The specific segments of interaction of 312C2 with other intracellular components may be identified by mutagenesis or direct biochemical means, e.g., cross-linking or affinity methods. Structural analysis by crystallographic or other physical methods will also be applicable. Further investigation of the mechanism of signal transduction will include study of associated components which may be isolatable by affinity methods or by genetic means, e.g., complementation analysis of mutants.

Further study of the expression and control of 312C2 will be pursued. The controlling elements associated with the antigens should exhibit differential physiological, developmental, tissue specific, or other expression patterns. Upstream or downstream genetic regions, e.g., control elements, are of interest. In particular, physiological or developmental variants, e.g., multiple alternatively processed forms of the mouse antigen have been found. See, e.g., SEQ ID NO: 1. Thus, differential splicing of message may lead to an assortment of membrane bound forms, soluble forms, and modified versions of antigen.

With human 312C2, 6 alternatively processed forms have been isolated. Clone A8, a truncated form of 312C2, is missing 7 amino acids immediately after the transmembrane domain. See SEQ ID NO: 6. Clone A5 is identical to 312C2 for the first 105 amino acids. It is believed that the divergence may be due to an unspliced intron. See SEQ ID NO: 7. Clone G10 is identical to 312C2 for the first 202 amino acids, but then varies in the 11 amino acids after the transmembrane domain and is 76 amino acids longer in the intracellular domain. The intracellular domain of G10, like that of 312C2, does not contain a death domain. See SEQ ID NO: 8.

Structural studies of the antigens will lead to design of new antigens, particularly analogs exhibiting agonist or antagonist properties on the molecule. This can be combined with previously described screening methods to isolate antigens exhibiting desired spectra of activities.

IV. Antibodies

Antibodies can be raised to various 312C2s, including species, polymorphic, or allelic variants, and fragments thereof, both in their naturally occurring forms and in their recombinant forms. Additionally, antibodies can be raised to 312C2s in either their active forms or in their inactive forms, including native or denatured versions. Anti-idiotypic antibodies are also contemplated.

Antibodies, including binding fragments and single chain versions, against predetermined fragments of the antigens can be raised by immunization of animals with conjugates of the fragments with immunogenic proteins. Monoclonal antibodies are prepared from cells secreting the desired antibody. These antibodies can be screened for binding to normal or defective 312C2s, or screened for agonistic or antagonistic activity, e.g., mediated through the antigen or its binding partner. Antibodies may be agonistic or antagonistic, e.g., by sterically blocking ligand binding. These monoclonal antibodies will usually bind with at least a $K_D$ of about 1 mM, more usually at least about 300 $\mu$M, typically at least about 100 $\mu$M, more typically at least about 30 $\mu$M, preferably at least about 10 $\mu$M, and more preferably at least about 3 $\mu$M or better.

The antibodies of this invention can also be useful in diagnostic applications. As capture or non-neutralizing antibodies, they can be screened for ability to bind to the antigens without inhibiting binding by a partner. As neutralizing antibodies, they can be useful in competitive binding assays. They will also be useful in detecting or quantifying 312C2 protein or its binding partners. See, e.g., Chan (ed.) (1987) Immunology: A Practical Guide, Academic Press, Orlando, Fla.; Price and Newman (eds.) (1991) Principles and Practice of Immunoassay, Stockton Press, N.Y.; and Ngo (ed.) (1988) Nonisotopic Immunoassay, Plenum Press, N.Y. Cross absorptions or other tests will identify antibodies which exhibit various spectra of specificities, e.g., unique or shared species specificities.

Further, the antibodies, including antigen binding fragments, of this invention can be potent antagonists that bind to the antigen and inhibit functional binding or inhibit the ability of a binding partner to elicit a biological response. They also can be useful as non-neutralizing antibodies and can be coupled to toxins or radionuclides so that when the antibody binds to antigen, a cell expressing it, e.g., on its surface, is killed. Further, these antibodies can be conjugated to drugs or other therapeutic agents, either directly or indirectly by means of a linker, and may effect drug targeting.

Antigen fragments may be joined to other materials, particularly polypeptides, as fused or covalently joined polypeptides to be used as immunogens. An antigen and its fragments may be fused or covalently linked to a variety of immunogens, such as keyhole limpet hemocyanin, bovine serum albumin, tetanus toxoid, etc. See Microbiology, Hoeber Medical Division, Harper and Row, 1969; Landsteiner (1962) Specificity of Serological Reactions, Dover Publications, New York; Williams, et al. (1967) Methods in Immunology and Immunochemistry, vol. 1, Academic Press, New York; and Harlow and Lane (1988) Antibodies: A Laboratory Manual, CSH Press, N.Y., for descriptions of methods of preparing polyclonal antisera.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) Basic and Clinical Immunology (4th ed.), Lange Medical Publications, Los Altos, Calif., and references cited therein; Harlow and Lane (1988) *Antibodies: A Laboratory Manual*, CSH Press; Goding (1986) *Monoclonal Antibodies: Principles and Practice* (2d ed.), Academic Press, New York; and particularly in Kohler and Milstein (1975) in *Nature* 256:495–497, which discusses one method of generating monoclonal antibodies.

Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," *Science* 246:1275–1281; and Ward, et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567; Moore, et al., U.S. Pat. No. 4,642,334; and Queen, et al. (1989) *Proc. Nat'l Acad. Sci. USA* 86:10029–10033.

The antibodies of this invention can also be used for affinity chromatography in isolating the protein. Columns can be prepared where the antibodies are linked to a solid support. See, e.g., Wilchek et al. (1984) *Meth. Enzymol.* 104:3–55.

Antibodies raised against each 312C2 will also be useful to raise anti-idiotypic antibodies. These will be useful in detecting or diagnosing various immunological conditions related to expression of the respective antigens.

V. Nucleic Acids

The described peptide sequences and the related reagents are useful in detecting, isolating, or identifying a DNA clone encoding 312C2, e.g., from a natural source. Typically, it will be useful in isolating a gene from mammal, and similar procedures will be applied to isolate genes from other species, e.g., warm blooded animals, such as birds and mammals. Cross hybridization will allow isolation of 312C2 from other species. A number of different approaches should be available to successfully isolate a suitable nucleic acid clone.

The purified protein or defined peptides are useful for generating antibodies by standard methods, as described above. Synthetic peptides or purified protein can be presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual*, Cold Spring Harbor Press. Alternatively, the 312C2 can be used as a specific binding reagent, and advantage can be taken of its specificity of binding, much like an antibody would be used.

For example, the specific binding composition could be used for screening of an expression library made from a cell line which expresses a 312C2. The screening can be standard staining of surface expressed antigen, or by panning. Screening of intracellular expression can also be performed by various staining or immunofluorescence procedures. The binding compositions could be used to affinity purify or sort out cells expressing the protein.

The peptide segments can also be used to predict appropriate oligonucleotides to screen a library. The genetic code can be used to select appropriate oligonucleotides useful as probes for screening. See, e.g., SEQ ID NO: 1 or 3. In combination with polymerase chain reaction (PCR) techniques, synthetic oligonucleotides will be useful in selecting correct clones from a library. Complementary sequences will also be used as probes, primers, or antisense strands. Based upon identification of the likely extracellular domain, various fragments should be particularly useful, e.g., coupled with anchored vector or poly-A complementary PCR techniques or with complementary DNA of other peptides.

This invention contemplates use of isolated DNA or fragments to encode a biologically active corresponding 312C2 polypeptides. See SEQ ID NO: 5. In addition, this invention covers isolated or recombinant DNA which encodes a biologically active, e.g., antigenic, protein or polypeptide which is capable of hybridizing under appropriate conditions with the DNA sequences described herein. Said biologically active protein or polypeptide can be an intact antigen, or fragment, and have an amino acid sequence disclosed in, e.g., SEQ ID NO: 2 or 4. Further, this invention covers the use of isolated or recombinant DNA, or fragments thereof, which encode proteins which are homologous to a 312C2 or which was isolated using cDNA encoding a 312C2 as a probe. The isolated DNA can have the respective regulatory sequences in the 5' and 3' flanks, e.g., promoters, enhancers, poly-A addition signals, and others.

An "isolated" nucleic acid is a nucleic acid, e.g., an RNA, DNA, or a mixed polymer, which is substantially separated from other components which naturally accompany a native sequence, e.g., ribosomes, polymerases, and/or flanking genomic sequences from the originating species. The term embraces a nucleic acid sequence which has been removed from its naturally occurring environment, and includes recombinant or cloned DNA isolates and chemically synthesized analogs or analogs biologically synthesized by heterologous systems. A substantially pure molecule includes isolated forms of the molecule. Generally, the nucleic acid will be in a vector or fragment less than about 50 kb, usually less than about 30 kb, typically less than about 10 kb, and preferably less than about 6 kb.

An isolated nucleic acid will generally be a homogeneous composition of molecules, but will, in some embodiments, contain minor heterogeneity. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, e.g., products made by transforming cells with any unnaturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site.

Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants. Alternatively, a heterologous promoter may be inserted upstream from a natural gene.

A significant "fragment" in a nucleic acid context is a contiguous segment of at least about 17 nucleotides, generally at least about 22 nucleotides, ordinarily at least about 29 nucleotides, more often at least about 35 nucleotides, typically at least about 41 nucleotides, usually at least about 47 nucleotides, preferably at least about 55 nucleotides, and in particularly preferred embodiments will be at least about 60 or more nucleotides.

A DNA which codes for a 312C2 protein will be particularly useful to identify genes, mRNA, and cDNA species which code for related or homologous proteins, as well as DNAs which code for homologs proteins from different species. There are likely homologues in other species, including primates, rodents, and birds. Various 312C2 proteins should be homologous and are encompassed herein. However, even proteins that have a more distant evolutionary relationship to the antigen can readily be isolated under appropriate conditions using these sequences if they are sufficiently homologous. Primate 312C2 proteins are of particular interest.

Recombinant clones derived from the genomic sequences, e.g., containing introns, will be useful for transgenic studies, including, e.g., transgenic cells and organisms, and for gene therapy. See, e.g., Goodnow (1992) "Transgenic Animals" in Roitt (ed.) *Encyclopedia of Immunology*, Academic Press, San Diego, pp. 1502–1504; Travis (1992) *Science* 256:1392–1394; Kuhn, et al. (1991) *Science* 254:707–710; Capecchi (1989) *Science* 244:1288; Robertson (1987)(ed.) *Teratocarcinomas and Embryonic Stem Cells: A Practical Approach*, IRL Press, Oxford; and Rosenberg (1992) *J. Clinical Oncology* 10:180–199.

Substantial homology in the nucleic acid sequence comparison context means either that the segments, or their complementary strands, when compared, are identical when optimally aligned, with appropriate nucleotide insertions or deletions, in at least about 50% of the nucleotides, generally at least about 58%, ordinarily at least about 65%, often at least about 71%, typically at least about 77%, usually at least about 85%, preferably at least about 95 to 98% or more, and in particular embodiments, as high as about 99% or more of the nucleotides. Alternatively, substantial homology exists when the segments will hybridize under selective hybridization conditions, to a strand, or its complement, typically using a sequence of 312C2, e.g., in SEQ ID NO: 1 or 3. Typically, selective hybridization will occur when there is at least about 55% homology over a stretch of at least about 30 nucleotides, preferably at least about 75% over a stretch of about 25 nucleotides, and most preferably at least about 90% over about 20 nucleotides. See, Kanehisa (1984) *Nuc. Acids Res.* 12:203–213. The length of homology comparison, as described, may be over longer stretches, and in certain embodiments will be over a stretch of at least about 17 nucleotides, usually at least about 28 nucleotides, typically at least about 40 nucleotides, and preferably at least about 75 to 100 or more nucleotides.

Stringent conditions, in referring to homology in the hybridization context, will be stringent combined conditions of salt, temperature, organic solvents, and other parameters, typically those controlled in hybridization reactions. Stringent temperature conditions will usually include temperatures in excess of about 30° C., usually in excess of about 37° C., typically in excess of about 55° C., preferably in excess of about 70° C. Stringent salt conditions will ordinarily be less than about 1000 mM, usually less than about 400 mM, typically less than about 250 mM, preferably less than about 150 mM. However, the combination of parameters is much more important than the measure of any single parameter. See, e.g., Wetmur and Davidson (1968) *J. Mol. Biol.* 31:349–370.

312C2 from other mammalian species can be cloned and isolated by cross-species hybridization of closely related species. Homology may be relatively low between distantly related species, and thus hybridization of relatively closely related species is advisable. Alternatively, preparation of an antibody preparation which exhibits less species specificity may be useful in expression cloning approaches.

VI. Making 312C2; Mimetics

DNA which encodes the 312C2 or fragments thereof can be obtained by chemical synthesis, screening cDNA libraries, or screening genomic libraries prepared from a wide variety of cell lines or tissue samples. See, e.g., Okayama and Berg (1982) *Mol. Cell. Biol.* 2:161–170; Gubler and Hoffman (1983) *Gene* 25:263–269; and Glover (ed.) (1984) *DNA Cloning: A Practical Approach*, IRL Press, Oxford. Alternatively, the sequences provided herein provide useful PCR primers or allow synthetic or other preparation of suitable genes encoding a 312C2; including, naturally occurring embodiments.

This DNA can be expressed in a wide variety of host cells for the synthesis of a full-length 312C2 or fragments which can in turn, e.g., be used to generate polyclonal or monoclonal antibodies; for binding studies; for construction and expression of modified molecules; and for structure/function studies.

Vectors, as used herein, comprise plasmids, viruses, bacteriophage, integratable DNA fragments, and other vehicles which enable the integration of DNA fragments into the genome of the host. See, e.g., Pouwels, et al. (1985 and Supplements) *Cloning Vectors: A Laboratory Manual*, Elsevier, N.Y.; and Rodriguez, et al. (1988)(eds.) *Vectors: A Survey of Molecular Cloning Vectors and Their Uses*, Buttersworth, Boston, Mass.

For purposes of this invention, DNA sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression. See e.g., Rodriguez, et al., Chapter 10, pp. 205–236; Balbas and Bolivar (1990) *Methods in Enzymology* 185:14–37; and Ausubel, et al. (1993) *Current Protocols in Molecular Biology*, Greene and Wiley, New York.

Representative examples of suitable expression vectors include pCDNA1; pCD, see Okayama, et al. (1985) *Mol. Cell Biol.* 5:1136–1142; pMC1neo Poly-A, see Thomas, et al. (1987) *Cell* 51:503–512; and a baculovirus vector such as pAC 373 or pAC 610. See, e.g., Miller (1988) *Ann. Rev. Microbiol.* 42:177–199.

It will often be desired to express a 312C2 polypeptide in a system which provides a specific or defined glycosylation pattern. See, e.g., Luckow and Summers (1988) *Bio/Technology* 6:47–55; and Kaufman (1990) *Meth. Enzymol.* 185:487–511.

The 312C2, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a. biologically active form, and allows purification by standard procedures of protein chemistry. See, e.g., Low (1989) *Biochim. Biophys. Acta* 988:427–454; Tse, et al. (1985) *Science* 230:1003–1008; and Brunner, et al. (1991) *J. Cell Biol.* 114:1275–1283.

Now that the 312C2 has been characterized, fragments or derivatives thereof can be prepared by conventional processes for synthesizing peptides. These include processes such as are described in Stewart and Young (1984) *Solid Phase Peptide Synthesis*, Pierce Chemical Co., Rockford, Ill.; Bodanszky and Bodanszky (1984) *The Practice of Peptide Synthesis*, Springer-Verlag, New York; Bodanszky (1984) *The Principles of Peptide Synthesis*, Springer-Verlag, New York; and Villafranca (ed.) (1991) *Techniques in Protein Chemistry II*, Academic Press, San Diego, Calif.

VII. Uses

The present invention provides reagents which will find use in diagnostic applications as described elsewhere herein, e.g., in the general description for T cell mediated conditions, or below in the description of kits for diagnosis. The antigen is useful as a marker, e.g., to identify T or NK cell subsets, or as a positive selection marker to fractionate immune subsets.

This invention also provides reagents with significant therapeutic value. The 312C2 (naturally occurring or recombinant), fragments thereof, and antibodies thereto, along with compounds identified as having binding affinity to 312C2, should be useful in the treatment of conditions associated with abnormal physiology or development, including abnormal proliferation, e.g., cancerous conditions, or degenerative conditions. In particular, modulation of development of lymphoid cells will be achieved by appropriate therapeutic treatment using the compositions provided herein. For example, a disease or disorder associated with abnormal expression or abnormal signaling by a 312C2 should be a likely target for an agonist or antagonist of the antigen. The antigen plays a role in regulation or development of hematopoietic cells, e.g., lymphoid cells, which affect immunological responses, e.g., autoimmune disorders.

In particular, the antigen will likely provide a costimulatory signal to T cell activation. Thus, the 312C2 will likely mediate T cell interactions with other cell types. These interactions lead, in particular contexts, to cell proliferation, enhanced cytokine synthesis by the cells, and consequential amplification of T cell proliferation.

Moreover, the 312C2 or antagonists could redirect T cell responses, e.g., towards a Th0/Th1 pathway, or towards a Th2 type response. Among these agonists should be various antibodies which recognize the appropriate epitopes, e.g., which mimic binding of 312C2 to its ligand. Alternatively, antibody antagonists may bind to epitopes which sterically can block partner binding.

Conversely, antagonists of 312C2, such as the naturally occurring secreted form of 312C2 or blocking antibodies, may provide a selective and powerful way to block immune responses in abnormal situations, e.g., autoimmune disorders, including rheumatoid arthritis, systemic lupus erythrematosis (SLE), Hashimoto's autoimmune thyroiditis, as well as acute and chronic inflammatory responses in which T cell activation, expansion, and/or immunological T cell memory play an important role. See also Samter, et al. (eds.) *Immunological Diseases* vols. 1 and 2, Little, Brown and Co. Suppression of T cell activation, expansion, and/or cytokine release by the naturally occurring secreted form of 312C2, which can be produced in large quantities by recombinant methods, or by blocking antibodies, should be effective in many disorders in which abnormal or undesired T cell responses are of importance, e.g., in a transplantation rejection situation.

In addition, certain combination compositions with other modulators of T cell signaling would be useful. Such other signaling molecules include TcR reagents, CD40, CD40L, CTLA-8, CD28, SLAM, FAS, and their respective antagonists.

Various abnormal conditions are known in each of the cell types shown to possess 312C2 mRNA by Northern blot analysis. See Berkow (ed.) *The Merck Manual of Diagnosis and Therapy*, Merck & Co., Rahway, N.J.; Thorn, et al. *Harrison's Principles of Internal Medicine*, McGraw-Hill, N.Y.; and Weatherall, et al. (eds.) *Oxford Textbook of Medicine*, Oxford University Press, Oxford. Many other medical conditions and diseases involve T cells or are T cell mediated, and many of these will be responsive to treatment by an agonist or antagonist provided herein. See, e.g., Stites and Terr (eds; 1991) *Basic and Clinical Immunology* Appleton and Lange, Norwalk, Conn.; and Samter, et al. (eds) *Immunological Diseases* Little, Brown and Co. These problems should be susceptible to prevention or treatment using compositions provided herein.

312C2 antibodies can be purified and then administered to a patient, veterinary or human. These reagents can be combined for therapeutic use with additional active or inert ingredients, e.g., in conventional pharmaceutically acceptable carriers or diluents, e.g., immunogenic adjuvants, along with physiologically innocuous stabilizers, excipients, buffers, or preservatives. These combinations can be sterile filtered and placed into dosage forms as by lyophilization in dosage vials or storage in stabilized aqueous preparations. This invention also contemplates use of antibodies or binding fragments thereof, including forms which are not complement binding. Sterile compositions of nucleic acids and proteins are also contemplated.

Drug screening using 312C2 or fragments thereof can be performed to identify compounds having binding affinity to or other relevant biological effects on 312C2 functions, including isolation of associated components. Subsequent biological assays can then be utilized to determine if the compound has intrinsic stimulating activity and is therefore a blocker or antagonist in that it blocks the activity of the antigen. Likewise, a compound having intrinsic stimulating activity can activate the signal pathway and is thus an agonist in that it simulates the activity of 312C2. This invention further contemplates the therapeutic use of blocking antibodies to 312C2 as antagonists and of stimulatory antibodies, e.g., A12, as agonists. This approach should be particularly useful with other 312C2 species variants.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) (1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Dosage ranges would ordinarily be expected to be in amounts lower than 1 mM concentrations, typically less than about 10 $\mu$M concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous or long term administration. See, e.g., Langer (1990) *Science* 249:1527–1533.

312C2, fragments thereof, and antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in many conventional dosage formulations. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, topical, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) (1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa.; Avis, et al. (eds.) (1993) *Pharmaceutical Dosage Forms: Parenteral Medications*, Dekker, N.Y.; Lieberman, et al. (eds.) (1990) *Pharmaceutical Dosage Forms: Tablets*, Dekker, N.Y.; and Lieberman, et al. (eds.) (1990) *Pharmaceutical Dosage Forms: Disperse Systems*, Dekker, N.Y. The therapy of this invention may be combined with or used in association with other agents, e.g., other modulators of T cell activation, e.g., CD40, CD40 ligand, CD28, CTLA-4, B7, B70, SLAM, T cell receptor signaling entities, or their respective antagonists.

Both the naturally occurring and the recombinant form of the 312C2s of this invention are particularly useful in kits and assay methods which are capable of screening compounds for binding activity to the proteins. Several methods of automating assays have been developed in recent years so as to permit screening of tens of thousands of compounds in a short period. See, e.g., Fodor, et al. (1991) *Science* 251:767–773, which describes means for testing of binding affinity by a plurality of defined polymers synthesized on a solid substrate. The development of suitable assays can be greatly facilitated by the availability of large amounts of purified, soluble 312C2 as provided by this invention.

Other methods can be used to determine the critical residues in the 312C2-312C2 ligand interactions. Mutational analysis can be performed, e.g., see Somoza, et al. (1993) *J. Exptl. Med.* 178:549–558, to determine specific residues critical in the interaction and/or signaling. Both extracellular domains, involved in the homophilic interaction, or intracellular domain, which provides interactions important in intracellular signaling.

For example, antagonists can normally be found once the antigen has been structurally defined, e.g., by tertiary structure data. Testing of potential interacting analogs is now possible upon the development of highly automated assay methods using a purified 312C2. In particular, new agonists and antagonists will be discovered by using screening techniques described herein. Of particular importance are compounds found to have a combined binding affinity for a spectrum of 312C2 molecules, e.g., compounds which can serve as antagonists for species variants of 312C2.

One method of drug screening utilizes eukaryotic or prokaryotic host cells which are stably transformed with recombinant DNA molecules expressing a 312C2. Cells may be isolated which express a 312C2 in isolation from other molecules. Such cells, either in viable or fixed form, can be used for standard binding partner binding assays. See also, Parce, et al. (1989) *Science* 246:243–247; and Owicki, et al. (1990) *Proc. Nat'l Acad. Sci. USA* 87:4007–4011, which describe sensitive methods to detect cellular responses.

Another technique for drug screening involves an approach which provides high throughput screening for compounds having suitable binding affinity to a 312C2 and is described in detail in Geysen, European Patent Application 84/03564, published on Sep. 13, 1984. First, large numbers of different small peptide test compounds are synthesized on a solid substrate, e.g., plastic pins or some other appropriate surface, see Fodor, et al. (1991). Then all the pins are reacted with solubilized, unpurified or solubilized, purified 312C2, and washed. The next step involves detecting bound 312C2.

Rational drug design may also be based upon structural studies of the molecular shapes of the 312C2 and other effectors or analogs. Effectors may be other proteins which mediate other functions in response to binding, or other proteins which normally interact with 312C2. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography*, Academic Press, New York. Structure from related TcR family genes will also provide further insight.

VIII. Kits

This invention also contemplates use of 312C2 proteins, fragments thereof, peptides, and their fusion products in a variety of diagnostic kits and methods for detecting the presence of another 312C2 or binding partner. Typically the kit will have a compartment containing either a defined 312C2 peptide or gene segment or a reagent which recognizes one or the other, e.g., 312C2 fragments or antibodies.

A kit for determining the binding affinity of a test compound to a 312C2 would typically comprise a test compound; a labeled compound, for example a binding partner or antibody having known binding affinity for 312C2; a source of 312C2 (naturally occurring or recombinant); and a means for separating bound from free labeled compound, such as a solid phase for immobilizing the molecule. Once compounds are screened, those having suitable binding affinity to the antigen can be evaluated in suitable biological assays, as are well known in the art, to determine whether they act as agonists or antagonists to the signaling pathway. The availability of recombinant 312C2 polypeptides also provide well defined standards for calibrating such assays. Histological analysis is also possible.

A preferred kit for determining the concentration of, e.g., a 312C2 in a sample would typically comprise a labeled compound, e.g., binding partner or antibody, having known binding affinity for the antigen, a source of antigen (naturally occurring or recombinant) and a means for separating the bound from free labeled compound, e.g., a solid phase for immobilizing the 312C2. Compartments containing reagents, and instructions, will normally be provided.

Antibodies, including antigen binding fragments, specific for the 312C2 or fragments are useful in diagnostic applications to detect the presence of elevated levels of 312C2 and/or its fragments. Such diagnostic assays can employ lysates, live cells, fixed cells, immunofluorescence, cell cultures, body fluids, and further can involve the detection of antigens related to the antigen in serum, or the like. Diagnostic assays may be homogeneous (without a separation step between free reagent and antigen-binding partner complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. See, e.g., Van Vunakis, et al. (1980) *Meth Enzymol.* 70:1–525; Harlow and Lane (1980) *Antibodies: A Laboratory Manual*, CSH Press, New York; and Coligan, et al. (eds.) (1993) *Current Protocols in Immunology*, Greene and Wiley, New York.

Anti-idiotypic antibodies may have similar use to diagnose presence of antibodies against a 312C2, as such may be diagnostic of various abnormal states. For example, overproduction of 312C2 may result in production of various immunological reactions which may be diagnostic of abnormal physiological states, particularly in proliferative cell conditions such as cancer or abnormal activation or differentiation.

Frequently, the reagents for diagnostic assays are supplied in kits, so as to optimize the sensitivity of the assay. For the subject invention, depending upon the nature of the assay, the protocol, and the label, either labeled or unlabeled antibody or binding partner, or labeled 312C2 is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay. Kits may be for solution determination, or histology in tissue samples.

Many of the aforementioned constituents of the drug screening and the diagnostic assays may be used without modification or may be modified in a variety of ways. For example, labeling may be achieved by covalently or non-covalently joining a moiety which directly or indirectly provides a detectable signal. In any of these assays, the binding partner, test compound, 312C2, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free 312C2, or alternatively the bound from the free test compound. The 312C2 can be immobilized on various matrixes followed by washing. Suitable matrixes include plastic such as an ELISA plate, filters, and beads. See, e.g., Coligan, et al. (eds.) (1993) *Current Protocols in Immunology*, Vol. 1, Chapter 2, Greene and Wiley, New York. Other suitable separation techniques include, without limitation, the fluorescein antibody magnetizable particle method described in Rattle, et al. (1984) *Clin. Chem.* 30:1457–1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of a 312C2. These sequences can be used as probes for detecting levels of the 312C2 message in samples from patients suspected of having an abnormal condition, e.g., cancer or developmental problem. Since the antigen is a marker for activation, it may be useful to determine the numbers of activated T cells to determine, e.g., when additional suppression may be called for. The preparation of both RNA and DNA nucleotide sequences, the labeling of the sequences, and the preferred size of the sequences has received ample description and discussion in the literature. See, e.g., Langer-Safer, et al. (1982) *Proc. Nat'l. Acad. Sci.* 79:4381–4385; Caskey (1987) *Science* 236:962–967; and Wilchek et al. (1988) *Anal. Biochem.* 171:1–32. Histological analysis may also be performed.

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89–97. Other kits may be used to evaluate T cell subsets, e.g., analysis or isolation, using conservative or destructive means.

IX. Methods for Isolating 312C2 Specific Binding Partners

The 312C2 protein should interact with a ligand based, e.g., upon its similarity in structure and function to other cell surface antigens exhibiting similar structure and cell type specificity of expression. Methods to isolate a ligand are made available by the ability to make purified 312C2 for screening programs. Soluble or other constructs using the 312C2 sequences provided herein will allow for screening or isolation of 312C2 specific ligands. Many methods exist for expression cloning, panning, affinity isolation, cross-linking, genetic selection, or other means to identify a receptor ligand.

A variety of different assays for detecting compounds capable of binding to 312C2 are used in the present invention. For instance, the binding of a test compound to 312C2 or a peptide fragment thereof can be measured directly, in the presence or absence of 312C2 polypeptide. This latter type of assay is called a direct binding assay. In addition, compounds which inhibit the binding of 312C2 to specific, preferably monoclonal, antibodies can be identified in competitive binding assays. Both direct binding assays and competitive binding assays can be used in a variety of different formats, similar to the formats used in immunoassays and receptor binding assays. For a description of different formats for binding assays, including competitive binding assays and direct binding assays, see *Basic and Clinical Immunology* 7th Edition (D. Stites and A. Terr ed.) 1991; *Enzyme Immunoassay*, E. T. Maggio, ed., CRC Press, Boca Raton, Fla. (1980); and "Practice and Theory of Enzyme Immunoassays," P. Tijssen, *Laboratory Techniques in Biochemistry and Molecular Biology*, Elsevier Science Publishers B.V. Amsterdam (1985), each of which is incorporated herein by reference.

In competitive binding assays, for example, the sample compound can compete with a labeled analyte for specific binding sites on a binding agent bound to a solid surface. In this type of format, the labeled analyte can be labeled 312C2 and the binding agent can be an antibody bound to a solid phase. Alternatively, the labeled analyte can be labeled antibody and the binding agent can be a solid phase wild type 312C2 or a fragment thereof. The concentration of labeled analyte bound to the capture agent is inversely proportional to the ability of a test compound to compete in the binding assay. The amount of inhibition of labeled analyte by the test compound depends on the binding assay conditions and on the concentrations of binding agent, labeled analyte, and test compound that are used. Under specified assay conditions, a compound is said to be capable of inhibiting the binding of 312C2 to a specific antibody in a competitive binding assay, if the amount of binding of the labeled analyte to the binding agent is decreased by 50% or preferably 90% or more. When a direct binding assay format is used, a test compound is said to bind an 312C2 when the signal measured is twice the background level or higher.

In a competitive binding assay, the sample compound competes with labeled protein for binding to a specific binding agent. As described above, the binding agent may be bound to a solid surface to effect separation of bound labeled protein from the unbound labeled protein. Alternately, the competitive binding assay may be conducted in liquid phase, and any of a variety of techniques known in the art may be used to separate the bound labeled protein from the unbound labeled protein. Following separation, the amount of bound labeled protein is determined. The amount of protein present in the sample is inversely proportional to the amount of labeled protein binding.

Alternatively, a homogeneous binding assay may be performed in which a separation step is not needed. In these type of binding assays, the label on the protein is altered by the binding of the protein to its specific binding agent. This alteration in the labeled protein results in a decrease or increase in the signal emitted by label, so that measurement of the label at the end of the binding assay allows for detection or quantitation of the protein.

The binding assay formats described herein employ labeled assay components. The label can be in a variety of forms. The label may be coupled directly or indirectly to the desired component of the assay according to methods well known in the art. A wide variety of labels may be used. The component may be labeled by any one of several methods. Traditionally, a radioactive label incorporating $^3$H, $^{125}$I, $^{35}$S, $^{14}$C, or $^{32}$P is used. Non-radioactive labels include ligands which bind to labeled antibodies, fluorophores, chemiluminescent agents, enzymes, and antibodies which can serve as specific binding pair members for a labeled ligand. The choice of label depends on sensitivity required, ease of conjugation with the compound, stability requirements, and available instrumentation. For a review of various labeling or signal producing systems which may be used, see U.S. Pat. No. 4,391,904, which is incorporated herein by reference.

Alternatively, an expression library can be screened for specific binding to 312C2, e.g., by cell sorting, or other screening to detect subpopulations which express such a binding component. See, e.g., Ho, et al. (1993) *Proc. Nat'l Acad. Sci. USA* 90:11267–11271. Alternatively, a panning method may be used. See, e.g., Seed and Aruffo (1987) *Proc. Nat'l Acad. Sci. USA* 84:3365–3369. A two-hybrid selection system may also be applied making appropriate constructs with the available 312C2 sequences. See, e.g., Fields and Song (1989) *Nature* 340:245–246.

The broad scope of this invention is best understood with reference to the following examples, which are not intended to limit the invention to specific embodiments.

EXAMPLES

General Methods

Some of the standard methods are described or referenced, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual* (2d ed.), vols. 1–3, CSH Press, New York; Ausubel, et al., Bioloay, Greene Publishing Associates, Brooklyn, N.Y.; or Ausubel, et al. (1987 and Supplements) *Current Protocols in Molecular Biology*, Greene and Wiley, New York; Innis, et al. (eds.)(1990) *PCR Protocols: A Guide to Methods and Applications*, Academic Press, New York. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Methods in Enzymology* vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, New York.; and Crowe, et al. (1992) *OIAexpress: The High Level Expression & Protein Purification System* QIAGEN, Inc., Chatsworth, Calif. Cell culture techniques are described in Doyle, et al. (eds.) (1994) *Cell and Tissue Culture: Laboratory Procedures*, John Wiley and Sons, New York.

Standard immunological techniques are described, e.g., in Hertzenberg, et al. (eds. 1996) *Weir's Handbook of Experimental Immunology* vols 1–4, Blackwell Science; Coligan (1991) *Current Protocols in Immunology* Wiley/Greene, New York; and *Methods in Enzymology* volumes. 70, 73, 74, 84, 92, 93, 108, 116, 121, 132, 150, 162, and 163.

Assays for vascular biological activities are well known in the art. They will cover angiogenic and angiostatic activities in tumor, or other tissues, e.g., arterial smooth muscle proliferation (see, e.g., Koyoma, et al. (1996) *Cell* 87:1069–1078), monocyte adhesion to vascular epithelium (see McEvoy, et al. (1997) *J. Exp. Med.* 185:2069–2077), etc. See also Ross (1993) *Nature* 362:801–809; Rekhter and Gordon (1995) *Am. J. Pathol.* 147:668–677; Thyberg, et al. (1990) *Atherosclerosis* 10:966–990; and Gumbiner (1996) *Cell* 84:345–357.

Assays for neural cell biological activities are described, e.g., in Wouterlood (ed. 1995) *Neuroscience Protocols* modules 10, Elsevier; *Methods in Neurosciences* Academic Press; and *Neuromethods* Humana Press, Totowa, N.J. Methodology of developmental systems is described, e.g., in Meisami (ed.) *Handbook of Human Growth and Developmental Biology* CRC Press; and Chrispeels (ed.) *Molecular Techniques and Approaches in Developmental Biology* Interscience.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y. Fluorescent labeling of appropriate reagents was performed by standard methods.

Example 1

Cloning of Mouse 312C2

Antibodies and flow-cytometric sorting

αβTcR+CD4–CD8–(DN) thymocytes were sorted using CD4/CD8a-PE and TcRαβ-FITC mAbs (PharMingen, San Diego, Calif.). See Zlotnik, et al. (1992) *J. Immunol.* 4:1211–1215. The sorted cells (approximately $5 \times 10^5$) were stimulated on solid-phase anti-CD3 for 24 h and were then expanded and cultured in IL-2 (500 U/ml) and IL-7 (100 U/ml) for one week (to approximately $1 \times 10^8$ cells). Cells were either harvested after one week in culture or stimulated again for 6 h on anti-CD3 and then harvested. See Kelner, et al. (1994) *Science* 266:1395–1399.

Construction of directional cDNA libraries

Poly (A)+ RNA from anti-CD3 stimulated αβDN thymocytes or unstimulated abDN thymocytes was used to synthesize first strand cDNA by using NotI/Oligo-dT primer (Gibco-BRL, Gaithersburg, Md.). Double-stranded cDNA was synthesized, ligated with BstXI adaptors, digested with NotI, size fractionated for >0.5 kilobase pairs (kb) and ligated into the NotI/BstXI sites of pJFE-14, a derivative of the pCDSRα vector. See Takebe, et al. *Mol. Cell Biol.* 8:466–472. Electro-competent *E. coli* DH10α cells (Gibco-BRL) were used for transformation. Total number of independent clones of the cDNA libraries were $1.2 \times 10^6$ for stimulated αβDN and $8 \times 10^5$ for unstimulated αβDN thymocytes, respectively.

Library subtraction

The PCR-based subtraction system developed by Wang and Brown (1991) *Proc. Natl. Acad. Sci. USA* 88:11505–11509, was modified to apply to plasmid cDNA libraries. A cDNA library specific for activated αβDN thymocytes was generated using 100 µg of the unstimulated αβDN cDNA library DNA digested with XbaI, NotI, and ScaI as driver DNA and 5 µg of the stimulated αβDN cDNA library DNA as tracer DNA. Following restriction digestion, the driver DNA was treated with DNA polymerase Klenow fragment to fill-in the restriction sites. After ethanol precipitation, the DNA was dissolved in 100 µl of water, heat-denatured and mixed with 100 µl (100 µg) of PHOTOPROBE™ biotin (Vector Laboratories, Burlingame, Calif.). The driver DNA was then irradiated with a 270-W sunlamp on ice for 20 min. 50 µl more PHOTOPROBE™ biotin was added and the biotinylation reaction was repeated. After butanol extraction, the photobiotinylated DNA (driver-U) was ethanol-precipitated and dissolved in 30 µl of 10 mM Tris-HCl and 1 mM EDTA, pH 8 (TE). As tracer DNA, 5 µg of stimulated αβDN cDNA was digested with XbaI and NotI; ethanol precipitated; and dissolved in 4 µl of TE (tracer-S). Tracer-S was mixed with 15 µl of driver-U, 1 µl (10 µg) of *E. coli* tRNA (Sigma, St. Louis, Mo.), and 20 µl of 2×hybridization buffer (1.5 M NaCl, 10 mM EDTA, 50 mM HEPES, pH 7.5, 0.2% SDS), overlaid with mineral oil, and heat-denatured. The sample tube was immediately transferred into a 68° C. water bath and incubated for 20 h. The reaction mixture was then subjected to streptavidin treatment followed by phenol/chloroform extraction. Subtracted DNA was precipitated, dissolved in 12 µl of TE, mixed with 8 µl of driver-U and 20 µl of 2×hybridization buffer, and then incubated at 68° C. for 2 h. After streptavidin treatment, the remaining DNA was ligated with 250 ng of a purified XbaI/NotI fragment of pJFE-14 and then transformed into electro-competent *E. coli* cells to generate the activation specific αβDN subtracted library (S1). 100 independent clones were randomly picked and screened by hybridization using a cocktail of known cytokine cDNAs. Plasmid DNA's were prepared from clones that did not hybridize to the cytokine probes. These clones were grouped by insert size and further characterized by DNA sequencing. Clones corresponding to the 312C2 were isolated.

Example 2

Cellular Expression of Mouse 312C2

A probe specific for cDNA encoding mouse 312C2 was used to determine tissue distribution of the antigen. All probes were labeled by random priming.

The results showed that 312C2 was expressed most abundantly in T cells, in particular, certain subsets of activated T cells. Thymus, spleen, and lymph node appeared to have more expression than other tissues. Expression levels are: thymus +; Th1 subset ++++; Th2 subset ++++, NK1.1+ T cells ++; αβ T cells ++; pro T cells +; CD4+ cells ++; CD8+ cells ++; and activated spleen cells +. A message was also detected in certain pro-, pre-, and mature B cell lines. The signal in the following cell types suggested that expression is very low to virtually absent in lung, heart, kidney, miacrophage, stroma, brain, liver, muscle, and testes.

Example 3

Purification of 312C2 Protein

Multiple transfected cell lines are screened for one which expresses the antigen at a high level compared with other cells. Various cell lines are screened and selected for their favorable properties in handling. Natural 312C2 can be isolated from natural sources, or by expression from a transformed cell using an appropriate expression vector. Purification of the expressed protein is achieved by standard procedures, or may be combined with engineered means for effective purification at high efficiency from cell lysates or supernatants. FLAG or $His_6$ segments can be used for such purification features.

By Northern analysis, it is clear that 312C2 is expressed in various Th1, Th2, CD4+, CD8+, NK1.1+, pro-, pre-, and αβCD4–CD8– T cells. 312C2 is also expressed in thymus and activated spleen cells. Cells expressing 312C2 typically contain a transcript of about 1.3 kb, corresponding to the size of the cloned 312C2 cDNA. Transcripts for 312C2 have not been detected in heart, kidney, macrophage, stroma, brain, liver, muscle, testes tissue.

The structural homology of 312C2 to the TNF receptor family, suggests a broad function of this molecule. 312C2, as an activation molecule, likely mediates enhanced Ag-specific proliferative responses on T cells, or induction of apoptosis of these cells. 312C2 agonists, or antagonists, may also act as a co-stimulatory molecule for T-cell activation, and may in fact, cause a shift of T helper cell types, e.g., from Th1 to Th2, or Th2 to Th1. Thus, 312C2 may be useful in the treatment of abnormal immune disorders, e.g., T cell immune deficiencies, chronic inflammation, or tissue rejection.

The mouse 312C12 protein exhibits structural features characteristic of a cell surface antigen. The protein is easily detected on particular cell types, others express lesser amounts. The 312C2 antigen should be present in the identified tissue types and the interaction of the antigen with its binding partner should be important for mediating various aspects of cellular physiology or development.

Example 4

Isolation of Homologous 312C2 Genes

The 312C2 cDNA can be used as a hybridization probe to screen a library from a desired source, e.g., a primate cell cDNA library. Many different species can be screened both for stringency necessary for easy hybridization, and for presence using a probe. Appropriate hybridization conditions will be used to select for clones exhibiting specificity of cross hybridization. Specifically, the mouse 312C2 cDNA clone was used to probe the HY06 human anergic T cell library. A clone of about 1006 bp encoding a predicted polypeptide of 241 amino acids was isolated.

Screening by hybridization using degenerate probes based upon the peptide sequences will also allow isolation of appropriate clones. Alternatively, use of appropriate primers for PCR screening will yield enrichment of appropriate nucleic acid clones. See SEQ ID NO: 5.

Similar methods are applicable to isolate either species, polymorphic, or allelic variants. Species variants are isolated using cross-species hybridization techniques based upon isolation of a full length isolate or fragment from one species as a probe.

Alternatively, antibodies raised against mouse 312C2 will be used to screen for cells which express cross-reactive proteins from an appropriate, e.g., cDNA library. The purified protein or defined peptides are useful for generating antibodies by standard methods, as described above. Synthetic peptides or purified protein are presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press. The resulting antibodies are used for screening, panning, or sorting.

Example 5

Expression and Tissue Distribution of Human 312C2

Southern and PCR analysis of various hematopoietic cells and tissues was performed as described above. Expression was detected in several cell lines and tissues, most notably, stimulated dendritic cell library, some activated T cell clones, activated PBMCs, NK clones, Th1, Th2 cells, pre-T cells, pro-T cells. Spleen and lung tissue had detectable levels of 312C2.

Example 6

Preparation of Antibodies Specific for 312C2

Synthetic peptides or purified protein are presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press. Polyclonal serum, or hybridomas may be prepared. In appropriate situations, the binding reagent is either labeled as described above, e.g., fluorescence or otherwise, or immobilized to a substrate for panning methods.

Example 7

Chromosomal Mapping of 312C2

Chromosome spreads are prepared. In situ hybridization is performed on chromosome preparations obtained from phytohemagglutinin-stimulated lymphocytes cultured for 72 h. 5-bromodeoxyuridine is added for the final seven hours of culture (60 μg/ml of medium), to ensure a posthybridization chromosomal banding of good quality.

An appropriate fragment, e.g., a PCR fragment, amplified with the help of primers on total B cell cDNA template, is cloned into an appropriate vector. The vector is labeled by nick-translation with $^3$H. The radiolabeled probe is hybridized to metaphase spreads as described in Mattei, et al. (1985) *Hum. Genet.* 69:327–331.

After coating with nuclear track emulsion (KODAK NTB$_2$), slides are exposed, e.g., for 18 days at 4° C. To avoid any slipping of silver grains during the banding procedure, chromosome spreads are first stained with buffered Giemsa solution and metaphase photographed. R-banding is then performed by the fluorochrome-photolysis-Giemsa (FPG) method and metaphases rephotographed before analysis.

Example 8

Isolation of Variants from Individuals

Mutational 312C2 variants from individuals having abnormal immune responses are isolated by standard methods. For example, affected cells, e.g., lymphocytes, are isolated as described, e.g., in Coligan (1991) *Current Protocols in Imunology* Wiley/Greene, New York. cDNA libraries are constructed as described above and probed with the mouse or human 312C2 clone. Isolated clones are then sequenced and compared to the human or mouse clone.

Alternatively, PCR techniques are also be employed to isolate variants. See, e.g., Innis, et al. (eds.)(1990) *PCR Protocols: A Guide to Methods and Applications*, Academic Press, New York.

Example 9

Immunohistochemical Localization

The antibody described in Example 6 is used to identify expression of 312C2 in various tissues. Methods for immunohistochemical staining are described, e.g., in Sheehan, et al. (eds.) (1987) *Theory and Practice of Histotechnology*, Battelle Press, Columbus, Ohio.

Example 10

Soluble Molecules

Soluble constructs of 312C2 are made, e.g., as described in Ausubel, et al. (1987 and Supplements) *Current Protocols* in *Molecular Biology*, Greene and Wiley, New York; and Coligan, et al. (eds.) (1995 and periodic supplements) *Current Protocols in Protein Science*, John Wiley and Sons, New York. Briefly, the transmembrane portion of 312C2 is truncated. The nucleic acid encoding the remaining portions of the molecule is subcloned into an appropriate vector and the protein expressed through a suitable host cell.

Many modifications and variations of this invention can be made without departing from its spirit and scope, as will be apparent to those skilled in the art. The specific embodiments described above are offered by way of example only, and the invention is to be limited only by the terms of the appended claims, along with the full scope of equivalents to which such claims are entitled. All references cited herein are incorporated herein by reference to the same extent as if each individual publication or patent application was specifically and individually indicated to be incorporated by reference.

What is claimed is:

1. An isolated or recombinant polynucleotide that:
   a) hybridizes under stringent hybridization conditions of at least 55° C. and less than 400 mM salt to the open reading frame of SEQ ID NO: 1 or 3; and
   b) encodes a polypeptide that:
      i) is expressed on activated T cells; and
      ii) specifically binds a polyclonal antibody generated against 12 contiguous amino acids of SEQ ID NO: 2 or 4.

2. A recombinant expression or replicating vector comprising the isolated or recombinant polynucleotide of claim 1.

3. A cell comprising the recombinant expression or replication vector of claim 2.

4. A kit comprising
   a) the isolated or recombinant polynucleotide of claim 1; and
   b) instructions for use or disposal of reagents in said kit.

5. A method of producing a polypeptide, comprising expressing the recombinant expression or replication vector of claim 2 in a host cell and isolating said polypeptide, thereby producing said polypeptide.

6. A recombinant or isolated polynucleotide of claim 1, that encodes at least 15 contiguous amino residues of SEQ ID NO: 4.

7. The isolated or recombinant polynucleotide of claim 6, that encodes at least 17 contiguous amino acid residues of SEQ ID NO: 4.

8. The isolated or recombinant polynucleotide of claim 6, which comprises:
   a) at least 57 contiguous nucleotides from the mature protein coding portion of SEQ ID NO: 1 or 3 that lacks an N terminal leader sequence; or
   b) is a variant due to the degeneracy of the genetic code.

9. The isolated or recombinant polynucleotide of claim 8, wherein:
   a) said contiguous nucleotides are from nucleotides 26–165 or nucleotides 191–241 of SEQ ID NO: 4.

10. The isolated or recombinant polynucleotide of claim 1, wherein said hybridization occurs over the entire open reading frame of SEQ ID NO: 1.

11. The isolated or recombinant polynucleotide of claim 1, wherein said polynucleotide is a variant due to the degeneracy of the genetic code.

12. The isolated or recombinant polynucleotide of claim 1, wherein said hybridization conditions are
   a) at least 60° C.;
   b) less than 150 mM salt; or
   c) both a) and b).

13. A method of producing a polynucleotide duplex comprising contacting the isolated or recombinant polynucleotide of claim 1 with a second polynucleotide for a time sufficient to produce said duplex under stringent hybridization conditions of at least 60° C. and less than 250 mM salt; thereby forming said duplex.

14. The polynucleotide of claim 1, which comprises:
   a) a sequence encoding a mature polypeptide of SEQ ID NO: 2 or 4, that lacks an N terminal leader sequence; or
   b) a sequence encoding an extracellular domain of SEQ ID NO: 2 or 4.

15. The polynucleotide of claim 1, which:
   a) comprises a sequence encoding a mature polypeptide coding portion of SEQ ID NO: 1 or 3, that does not encode an N terminal leader sequence; or
   b) comprises a sequence encoding an intracellular domain of SEQ ID NO: 2 or 4.

16. The isolated or recombinant polynucleotide of claim 1, which:
   a) is attached to a solid substrate; or
   b) is detectably labeled.

17. The isolated or recombinant polynucleotide of claim 1, in a sterile composition.

18. The isolated or recombinant polynucleotide of claim 17, that encodes at least 21 contiguous amino add residues.

19. The isolated or recombinant polynucleotide of claim 1, wherein the isolated polynucleotide, synthetically produced.

20. The isolated or recombinant polynucleotide of claim 19, that encodes at least 21 contiguous amino acid residues.

21. The isolated or recombinant polynucleotide of claim 1, that encodes an antigenic polypeptide having at least 12 contignous amino acid residues.

22. The isolated or recombinant polynucleotide of claim 21, wherein said contiguous amino acid residues number at least 21.

23. An isolated or recombinant polynucleotide encoding a polypeptide that
   has a conservative amino add substitution of a mature polypeptide of SEQ ID NO: 2 or 4 that lacks an N terminal leader sequence.

24. The isolated or recombinant polynucleotide of claim 23, comprising a sequence of from SEQ ID NO: 3.

25. The isolated or recombinant polynucleotide of claim 23, comprising:
   a) nucleotides 124 to 751 of SEQ ID NO: 1; or
   b) nucleotides 54 to 723 of SEQ ID NO: 3.

26. A method of producing a polynucleotide duplex comprising contacting the isolated or recombinant polynucleotide of claim 23 with a second polynucleotide for a time sufficient to produce said duplex under stringent hybridization conditions of at least 60° C. and less than 250 mM salt; thereby forming said duplex.

27. A recombinant expression or replicating vector comprising the isolated or recombinant polynucleotide of claim 23.

28. A cell comprising the recombinant expression or replication vector of claim 27.

29. A method of producing an antigenic polypeptide, comprising expressing the recombinant expression or replication vector of claim 27 in a host cell and isolating said antigenic polypeptide, thereby producing said antigenic polypeptide.

30. A recombinant or isolated polynucleotide that hybridizes to the open reading frame of SEQ ID NO: 1 or 3 under stringent hybridization and wash conditions of at least 55° C., a salt concentration of less than 250 mM, and 50% formamide.

31. A recombinant expression or replicating vector comprising:
   a) said polynucleotide of claim 30; or
   b) a polynucleotide sequence encoding the mature polypeptide of SEQ ID NO: 4 that lacks an N terminal leader sequence.

32. A cell comprising the recombinant expression or replication vector of claim 31.

33. A method of producing an antigenic polypeptide, comprising expressing the recombinant expression or replication vector of claim 32 in a host cell and isolating said polypeptide, thereby producing said polypeptide.

34. A method of producing a polynucleotide duplex comprising contacting said polynucleotide of claim 30 with a second polynucleotide for a time sufficient to produce said duplex under stringent hybridization conditions of at least 60° C. and less than 250 mM salt; thereby forming said duplex.

35. The polynucleotide of claim 30:
   a) wherein said hybridization conditions are at least 70° C.; or
   b) comprises at least 36 contiguous nucleotides of the mature coding portion of SEQ ID NO: 1 or 3 that does not encode an N terminal leader sequence.

36. The polynucleotide of claim 30 comprising
   a polynucleotide sequence encoding an antigenic polypeptide of at least 20 contiguous amino acids of the mature SEQ ID NO: 4 polypeptide that lacks an N terminal leader sequence.

* * * * *